US008598254B2

(12) United States Patent
Tada et al.

(10) Patent No.: US 8,598,254 B2
(45) Date of Patent: Dec. 3, 2013

(54) BINDING METHOD OF WATER ABSORBENT RESIN

(75) Inventors: Kenji Tada, Hyogo (JP); Kenji Kadonaga, Hyogo (JP); Masazumi Sasabe, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 455 days.

(21) Appl. No.: 12/673,425

(22) PCT Filed: Sep. 4, 2008

(86) PCT No.: PCT/JP2008/066371
§ 371 (c)(1),
(2), (4) Date: Feb. 12, 2010

(87) PCT Pub. No.: WO2009/031701
PCT Pub. Date: Mar. 12, 2009

(65) Prior Publication Data
US 2011/0237739 A1 Sep. 29, 2011

(30) Foreign Application Priority Data
Sep. 7, 2007 (JP) ................. 2007-233394

(51) Int. Cl.
*C08J 3/03* (2006.01)
*C08K 3/20* (2006.01)
*C08K 5/05* (2006.01)
*C08G 69/48* (2006.01)

(52) U.S. Cl.
USPC ............... 523/326; 523/402; 523/501; 524/1; 524/60; 524/475; 524/608; 524/767

(58) Field of Classification Search
USPC ........ 524/1, 60, 475, 608, 767; 523/326, 402, 523/501
See application file for complete search history.

(56) References Cited

U.S. PATENT DOCUMENTS

| | | | |
|---|---|---|---|
| 4,507,473 A | 3/1985 | Bernert et al. | |
| 4,734,478 A | 3/1988 | Tsubakimoto et al. | |
| 4,755,562 A | 7/1988 | Alexander et al. | |
| 4,783,510 A | 11/1988 | Saotome | |
| 4,824,901 A | 4/1989 | Alexander et al. | |
| 5,064,582 A | 11/1991 | Sutton et al. | |
| 5,115,011 A * | 5/1992 | Harada et al. | 524/419 |
| 5,140,076 A | 8/1992 | Hatsuda et al. | |
| 5,206,205 A | 4/1993 | Tsai | |
| 5,264,495 A | 11/1993 | Irie et al. | |
| 5,422,405 A | 6/1995 | Dairoku et al. | |
| 5,610,208 A | 3/1997 | Dairoku et al. | |
| 5,672,633 A | 9/1997 | Brehm et al. | |
| 6,071,976 A | 6/2000 | Dairoku et al. | |
| 6,133,193 A | 10/2000 | Kajikawa et al. | |
| 6,228,930 B1 | 5/2001 | Dairoku et al. | |
| 6,239,230 B1 | 5/2001 | Eckert et al. | |
| 6,265,488 B1 | 7/2001 | Fujino et al. | |
| 6,297,319 B1 | 10/2001 | Nagasuna et al. | |
| 6,300,423 B1 | 10/2001 | Engelhardt et al. | |
| 6,372,852 B2 | 4/2002 | Hitomi et al. | |
| 6,458,921 B1 | 10/2002 | Dairoku et al. | |
| 6,472,478 B1 | 10/2002 | Funk et al. | |
| 6,514,615 B1 | 2/2003 | Sun et al. | |
| 6,559,239 B1 | 5/2003 | Riegel et al. | |
| 6,605,673 B1 | 8/2003 | Mertens et al. | |
| 6,620,899 B1 | 9/2003 | Morken et al. | |
| 6,657,015 B1 | 12/2003 | Riegel et al. | |
| 6,720,389 B2 | 4/2004 | Hatsuda et al. | |
| 6,809,158 B2 | 10/2004 | Ikeuchi et al. | |
| 6,875,511 B2 | 4/2005 | Dairoku et al. | |
| 7,288,601 B2 | 10/2007 | Nogi et al. | |
| 8,349,913 B2 | 1/2013 | Harren et al. | |
| 2001/0025093 A1 | 9/2001 | Ishizaki et al. | |
| 2002/0061978 A1 | 5/2002 | Hatsuda et al. | |
| 2003/0008946 A1 | 1/2003 | Dairoku et al. | |
| 2004/0106745 A1 | 6/2004 | Nakashima et al. | |
| 2004/0240316 A1 | 12/2004 | Nogi et al. | |
| 2005/0048221 A1 | 3/2005 | Irie et al. | |
| 2006/0057389 A1 | 3/2006 | Reimann et al. | |
| 2006/0276598 A1 | 12/2006 | Wada et al. | |
| 2007/0149760 A1 | 6/2007 | Kadonaga et al. | |
| 2008/0227932 A1 | 9/2008 | Funk et al. | |

FOREIGN PATENT DOCUMENTS

| | | |
|---|---|---|
| CN | 1572820 | 2/2005 |
| CN | 1784430 | 6/2006 |
| EP | 603292 | 6/1994 |

(Continued)

OTHER PUBLICATIONS

Machine translation of JP 2005-054151 A; Miyake et al; Mar. 2005.*

(Continued)

*Primary Examiner* — Karuna P Reddy
(74) *Attorney, Agent, or Firm* — Roylance, Abrams, Berdo & Goodman, L.L.P.

(57) ABSTRACT

Aqueous liquid and moisture vapor are added to water absorbent resin powder so that particles of the water absorbent resin powder are bound. Supplying the aqueous liquid and moisture vapor to the water absorbent resin powder reduces the amount of particles that remain unbound (ungranulated) and increases the concentration of the water absorbent resin bound particles to provide improved drying efficiency and to obtain particulate water absorbent resin having excellent properties even when the bound particles are highly concentrated. The present invention provides (i) a method for binding water absorbent resin and (ii) a method for producing particulate water absorbent resin including the step of binding particles of water absorbent resin powder.

10 Claims, 5 Drawing Sheets

(56) References Cited

FOREIGN PATENT DOCUMENTS

| | | |
|---|---|---|
| EP | 0885917 | 12/1998 |
| EP | 1400556 | 3/2004 |
| EP | 1712584 A2 * | 10/2006 |
| EP | 1824910 | 8/2007 |
| JP | 52002877 | 1/1977 |
| JP | 63-99211 | 4/1988 |
| JP | 1-113406 | 5/1989 |
| JP | 1-297430 | 11/1989 |
| JP | 2-160814 | 6/1990 |
| JP | 3-152104 | 6/1991 |
| JP | 4-214734 | 8/1992 |
| JP | 4-227705 | 8/1992 |
| JP | 7-224204 | 8/1995 |
| JP | 7-242709 | 9/1995 |
| JP | 11-349625 | 12/1999 |
| JP | 2000-189794 | 7/2000 |
| JP | 2002-121291 | 4/2002 |
| JP | 2002-201290 | 7/2002 |
| JP | 2004-352940 | 12/2004 |
| JP | 2004-352941 | 12/2004 |
| JP | 2005054151 | 3/2005 |
| JP | 2005-97585 | 4/2005 |
| JP | 2008-38128 | 2/2008 |
| WO | 2004/037900 | 5/2004 |
| WO | 2008/141821 | 11/2008 |

OTHER PUBLICATIONS

European Search Report dated Jul. 26, 2011 of European Application No. 08829802.1.

International Search Report for PCT/JP2010/001521 dated May 25, 2010.

Chinese Office Action dated Nov. 13, 2012, from the Chinese Patent Office in Chinese Application No. 201080010035.3, and partial English translation.

US Office Action dated Feb. 28, 2013, from the U.S. Patent and Trademark Office in U.S. Appl. No. 13/254,573.

Supplementary European Search Report for EP 10748535.1, dated Mar. 16, 2013.

Chinese Office Action for CN 201080010035.3, dated Apr. 2, 2013, and English translation thereof.

* cited by examiner (a)

(b)

(c)

BINDING METHOD OF WATER ABSORBENT RESIN

TECHNICAL FIELD

The present invention relates to a method for binding water absorbent resin. More specifically, the present invention relates to (i) a method for binding water absorbent resin in which its solid content concentration of bound particles obtained by adding aqueous liquid and moisture vapor to water absorbent resin powder is increased and granulation strength and absorbent property of particulate water absorbent resin are enhanced, that is, a method for binding water absorbent resin which method allows a drying efficiency to be improved by increasing an amount of a solid content of the water absorbent resin, and (ii) a water absorbent resin production method which includes a step of binding particles of water absorbent resin powder.

BACKGROUND ART

Conventionally, water absorbent resin has been widely used to constitute sanitary materials such as a disposable diaper, a sanitary napkin, an incontinence pad, and the like, so as to absorb aqueous liquid such as body fluid and the like. Further, water absorbent resin has been used also to constitute water absorbing articles for horticulture, agriculture, and the like.

Further, it is known that, in view of a handling property, safety, and hygiene, particles of the water absorbent resin powder are granulated (bound) by using water, aqueous liquid, water-soluble polymer, or the like so as to have a desired particle diameter so that the resultant is used as a water absorbing agent or the like. Further, it is known that: water, aqueous liquid, and the like are added to a deposition of the water absorbent resin powder which deposition has appropriate thickness so as to obtain a sheet-shaped water absorbent resin layer, and then the resultant is granulated so as to have a desired particle diameter, thereby producing a water absorbing agent or the like.

However, according to the conventional granulation method, also after the granulation, a large amount of ungranulated water absorbent resin powder (particularly, powder whose particle diameter is less than 150 μm) remains. Thus, in case of using the resultant water absorbing agent and the like in a disposable diaper and the like, its liquid permeability drops. Further, in case of improving properties such as absorbency against pressure or a similar property by further surface crosslinking the granulated water absorbing agent or the like, the ungranulated powder preferentially absorbs the surface crosslinking agent, so that it is impossible to evenly disperse the surface crosslinking agent over whole the water absorbing agent or the like. As a result, it is difficult to obtain the water absorbing agent or the like which satisfies the desired property (quality) level.

Further, in case of granulating the water absorbent resin powder by adding water, aqueous liquid, or the like, it is necessary to add a large amount of water, aqueous liquid, water-soluble polymer, or the like so as to realize sufficient granulation, so that the energy cost increases at the subsequent drying step. In case of granulating the water absorbent resin powder by adding various kinds of binder such as water-soluble polymer or the like, the binder itself causes the liquid permeability, absorbent property, and the like of the resultant water absorbing agent to drop.

As a method for solving the problems of the conventional granulation method, Patent Document 1 describes a production method of particulate water absorbent resin. According to the method, when supplying water to water absorbent resin powder so as to carry out granulation, it is possible to reduce an amount of ungranulated particles after the granulation and it is possible to reduce also the drying cost after the granulation by suppressing an amount of supplied water required in the granulation. Specifically, Patent Document 1 describes "a method for producing particulate water absorbent resin comprises the steps of: supplying moisture to water absorbent resin powder so as to bind particles of the powder; and obtaining granulated water absorbent resin particles from the bound particles of the powder, wherein the supplied moisture is in a form of moisture vapor".

Further, Patent Document 2 describes a method in which: water absorbent resins are made gelatinous with a large amount of warm water so as to cause the water absorbent resins to adhere to each other, and evaporation energy of the large amount of water is used to dry the gelatinous water absorbent resins. Specifically, Patent Document 2 describes "a method for producing a granulated water absorbent resin by mixing water absorbent resin powder and aqueous liquid comprises the steps of: heating the aqueous liquid which has not been mixed; and mixing the heated water and the water absorbent resin powder at a high speed".

[Patent Document 1]
   Japanese Unexamined Patent Publication Tokukai 2005-54151 (Publication date: Mar. 3, 2005)
[Patent Document 2]
   Japanese Unexamined Patent Publication Tokukaihei 11-106514 (Publication date: Apr. 20, 1999)

DISCLOSURE OF INVENTION

However, as a result of diligent study carried out by the present inventors, they found that: in case of granulating water absorbent resin, particularly, fine-powdery water absorbent resin as the aforementioned powder, its surface area is large, so that a water absorption rate is high, which results in difficulty in evenly adding a liquid binder such as aqueous liquid or the like for example. Thus, conventionally, a fluid bed used in granulation or a stirring mixer such as a high speed stirring mixer raises such problem that: in case where an amount of aqueous liquid added to the granulated water absorbent resin exceeds 50%, mixture of the water absorbent resin and the aqueous liquid is extremely uneven, so that it is extremely difficult to continuously and stably carry out the mixture. Also, such device raises such problem that uneven addition of the aqueous liquid causes the property to drop and causes the granulated resultant to be broken. Further, the present inventors found that: in case of the production method including the step of granulating particles of powder, a certain amount of moisture retained in the granulated resultant causes the productivity to drop due to a load in the drying step and extension of the drying time.

In case where the amount of aqueous liquid added to the granulated water absorbent resin is less than 50%, powder adheres to an internal part of the stirring mixer, particularly, to stirring vanes due to its adhesive force, so that the powder remains in the device and the remaining powder cannot be discharged. Particularly, in case where 50 wt % or more of fine powder (powder) whose particle diameter is 105 μm or less is included in the water absorbent resin, it is extremely difficult to carry out industrial granulation.

The present invention was made in view of the foregoing conventional problems, and an object of the present invention is to provide a binding method by which it is possible to continuously and stably carry out granulation for a long time and it is possible to obtain a granulated product having excellent granulation strength.

According to the granulation (binding) method of water absorbent resin which method is described in Patent Document 1, moisture in a form of moisture vapor is supplied to water absorbent resin powder so that particles of the powder are bound. This raises such problem that a long time and a large amount of moisture vapor are required. Further, Patent Document 1 does not describe any Example adopting the continuous mode.

Further, the granulation method of water absorbent resin which method is described in Patent Document 2 does not mention, as specific Examples, a case where the water absorbent resin is highly concentrated, that is, a case where a solid content of the water absorbent resin is large, e.g., a case where the solid content of the water absorbent resin is 50 wt % or more.

Further, according to the production method of the granulated (bound) water absorbent resin which method is described in Patent Document 2, it is not easy to evenly supply aqueous liquid to whole the water absorbent resin powder, and it is necessary to use an excessive amount of moisture, which raises such problem that the energy cost in the subsequent drying step increases.

The present invention was made in view of the problems of Patent Documents 1 and 2, and an object of the present invention is to provide (i) a binding (granulation) method of water absorbent resin which method makes it possible to improve a drying efficiency by increasing a concentration of the water absorbent resin, i.e., by increasing a solid content of the water absorbent resin and makes it possible to obtain particulate water absorbent resin having excellent property even in case where the water absorbent resin is highly concentrated, i.e., even in case where a large amount of solid content is included in the water absorbent resin and (ii) a production method of particulate water absorbent resin which method comprises the step of binding (granulating) particles of water absorbent resin powder.

In order to solve the foregoing problems, a method of the present invention for binding water absorbent resin comprises the step of adding aqueous liquid and moisture vapor to water absorbent resin powder so as to bind particles of the water absorbent resin powder.

According to the invention, the method of the present invention for binding water absorbent resin includes the step of adding aqueous liquid and moisture vapor to water absorbent resin powder, so that it is possible to more evenly supply moisture to whole the powder than the case of adding only the aqueous liquid. This makes it possible to suppress an amount of the supplied moisture. Thus, it is possible to reduce the drying time at the drying step after binding the particles of the water absorbent resin powder. As a result, the method of the present invention for binding water absorbent resin makes it possible to improve the productivity of particulate water absorbent resin.

Further, according to the present invention, the method of the present invention for binding water absorbent resin includes the step of adding aqueous liquid and moisture vapor to water absorbent resin powder, so that it is possible to more firmly bind the particles of the powder with the aqueous liquid than the case of adding only the moisture vapor. Further, it is possible to bind the particles of the powder with less voids of the bound powder with moisture vapor. This makes it possible to more firmly clump and bind the particles of the water absorbent resin powder in binding the water absorbent resin powder. As a result, the method of the present invention for binding water absorbent resin makes it possible to obtain particulate water absorbent resin having excellent properties, particularly, excellent damage resistance.

Further, it is preferable to arrange the method of the present invention for binding water absorbent resin so that the particles of the water absorbent resin powder are continuously bound.

As a result, the method of the present invention for binding water absorbent resin makes it possible to further improve the productivity of the particulate water absorbent resin.

Herein, in case where the water absorbent resin after binding the water absorbent resin powder is highly concentrated, an amount of binder such as water decreases in the water absorbent resin, so that a cohesive force thereof drops. As a result, the property may drop. However, the aqueous liquid is added in the method of the present invention for binding water absorbent resin, so that the aqueous liquid serves as the binder. As a result, even in case where the water absorbent resin after binding the particles of the water absorbent resin powder is highly concentrated, it is possible to realize the same property of particulate water absorbent resin as that in case where the water absorbent resin is less concentrated, e.g., that in case where the solid content of the water absorbent resin is 49 wt % or less.

Further, it is preferable to arrange the method of the present invention for binding water absorbent resin so that 50 to 10 parts by weight of the aqueous liquid is added to 50 to 90 parts by weight of the water absorbent resin powder so that a total amount is 100 parts by weight.

Thus, the method of the present invention for binding water absorbent resin makes it possible to highly concentrate the water absorbent resin after binding the particles of the water absorbent resin powder.

Further, it is preferable to arrange the method of the present invention for binding water absorbent resin so that 1 to 100 kg/hr of the moisture vapor is added to 100 kg/hr of the water absorbent resin powder.

According to the method of the present invention for binding water absorbent resin, most of the added moisture vapor is discharged without being incorporated into the water absorbent resin powder. As a result, the solid content of the water absorbent resin after binding the particles of the water absorbent resin powder does not decrease.

Further, it is preferable to arrange the method of the present invention for binding water absorbent resin so that the particles of the water absorbent resin powder are bound by using a rotation disk mixer.

As a result, the method of the present invention for binding water absorbent resin makes it possible to stir and mix the particles of the water absorbent resin powder by a centrifugal force and a gravity.

Further, the method of the present invention for binding water absorbent resin may be arranged so that the water absorbent resin powder includes powder of water absorbent resin whose surface has been crosslinked.

In order to solve the foregoing problems, a method of the present invention for producing particulate water absorbent resin comprises the step of adding aqueous liquid and moisture vapor to water absorbent resin powder so as to bind particles of the water absorbent resin powder.

According to the invention, the method of the present invention for producing particulate water absorbent resin includes the step of adding aqueous liquid and moisture vapor to water absorbent resin powder, so that it is possible to more evenly supply moisture to whole the powder than the case of adding only the aqueous liquid. This makes it possible to suppress an amount of the supplied moisture. Thus, it is possible to reduce the drying time at the drying step after binding the water absorbent resin powder. As a result, the method of the present invention for producing particulate water absorbent resin makes it possible to improve the productivity of particulate water absorbent resin.

Further, according to the invention, the method of the present invention for producing particulate water absorbent resin includes the step of adding aqueous liquid and moisture vapor to water absorbent resin powder, so that it is possible to more firmly bind the particles of the powder with the aqueous liquid than the case of adding only the moisture vapor. Further, the moisture vapor can bind the particles of the powder with less voids of the bound powder. This makes it possible to more firmly clump and bind the particles of the water absorbent resin powder in binding the water absorbent resin powder. As a result, the method of the present invention for producing particulate water absorbent resin makes it possible to obtain particulate water absorbent resin having excellent properties, particularly, excellent damage resistance.

Further, it is preferable to arrange the method of the present invention for producing particulate water absorbent resin so as to include plural steps of binding the particles of the water absorbent resin powder.

As a result, the method of the present invention for producing particulate water absorbent resin makes it possible to further improve the productivity and the quality of the particulate water absorbent resin.

Further, it is preferable to arrange the method of the present invention for producing particulate water absorbent resin so that a solid content of the water absorbent resin powder whose particles have been bound ranges from 50 to 90 wt %.

As a result, the method of the present invention for producing particulate water absorbent resin makes it possible to increase the concentration of the water absorbent resin after binding the particles of the water absorbent resin powder. Thus, it is possible to surely reduce a drying time in the drying step after binding the particles of the water absorbent resin powder. As a result, the method of the present invention for producing particulate water absorbent resin makes it possible to surely improve the productivity of the particulate water absorbent resin.

Additional objects, features, and strengths of the present invention will be made clear by the description below. Further, the advantages of the present invention will be evident from the following explanation in reference to the drawings.

REFERENCE NUMERALS

Figure 1:
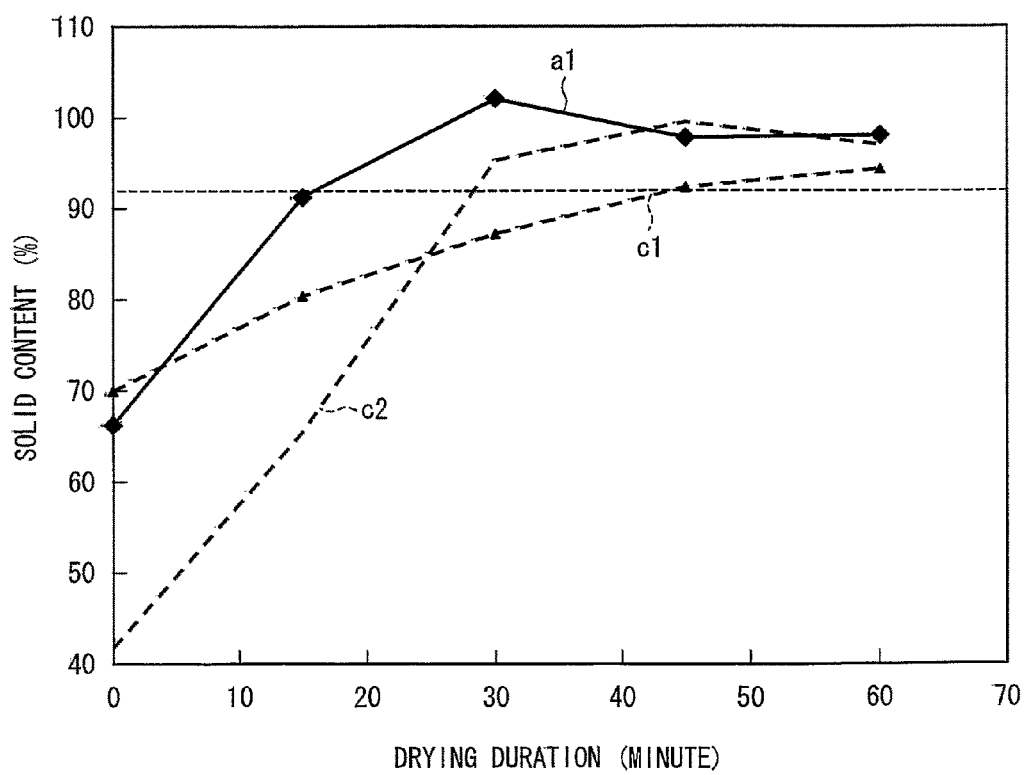
FIG. 1 is a graph showing a solid content of water absorbent resin obtained according to an embodiment of a method of the present invention for binding water absorbent resin and a solid content of water absorbent resin obtained according to a conventional method for binding water absorbent resin.

10 Plastic supporting cylinder
11 400 mesh stainless metal gauze
12 Water absorbent resin particles (water absorbent resin)
13 Piston
14 Load (weight)
15 Petri dish
16 Glass filter
17 Filter paper
18 0.90 mass % physiological saline
31 Tank
32 Glass tube
33 0.69 mass % physiological saline
34 L-shaped tube with a cock
35 Cock
40 Container
41 Cell
42 Stainless metal gauze
43 Stainless metal gauze
44 Swollen gel (gel)
45 Glass filter
46 Piston
47 Hole
48 Collecting container
49 Even scale
51 Horizontal continuous mixer
52 Casing
53 Inlet
54 Inlet
55 Inlet
58 Inlet
60 Outlet
61 Rotational axis
62 Stirring vane

BEST MODE FOR CARRYING OUT THE INVENTION

The following description will detail the present invention, but the scope of the present invention is not limited to this, and the invention may be altered in many variations within the spirit of the present invention. Specifically, the present invention is not limited to the following embodiment, but may be altered in many variations within the scope of claims. That is, an embodiment based on a proper combination of technical means disclosed in different embodiments is encompassed in the technical scope of the present invention. Note that, in the present specification, "mass" is a synonymous of "weight". Further, such wording that "ranges (ranging) from A to B" refers to such condition that "not less than A and not more than B". Further, "particle diameter" is synonymous of "particle size".

In the present invention, an amount of water absorbent resin powder to be supplied, an amount of particulate water absorbent resin to be produced, an amount of aqueous liquid or moisture vapor to be discharged, a rotation rate of each stirring vane of a production device, and a similar value are suitably set to optimal conditions in accordance with a type of the device.

A method of the present invention for binding water absorbent resin includes the step of adding aqueous liquid and moisture vapor to water absorbent resin powder so as to bind particles of the water absorbent resin powder. Further, it is preferable to arrange the method for binding water absorbent resin so that the particles of the water absorbent resin powder are continuously bound.

The water absorbent resin used in the present invention includes 10 wt % or less of water with respect to whole the water absorbent resin. The water absorbent resin powder used in the present invention is not particularly limited as long as the powder is made of water absorbent resin. Further, the water absorbent resin powder used in the present invention includes also water absorbent resin fine particles having been removed at the step of classifying particulate water absorbent resin into particles each of which has a desired particle diameter. Further, the aqueous liquid used in the present invention is not particularly limited as long as the liquid is aqueous.

That is, suitable aqueous liquid is selected in accordance with a type of powder to be used and purpose of use of a granulated resultant. Examples thereof include: water; aqueous liquid containing water-soluble salt or hydrophilic organic solvent and the like; and a similar aqueous liquid. As the liquid binder, it is preferable to use water or aqueous liquid in view of property, granulation strength, efficiency, safety, production cost, and the like. An amount of water is 90 wt % or more, preferably 99 wt % or more, more preferably ranges from 99 to 100 wt %. It is particularly preferable that the liquid binder is made only of water. Further, water-insoluble inorganic or organic fine particles may be dispersed in the aqueous liquid. Further, in case of using water absorbent resin powder as the aforementioned powder, the liquid binder may include an organic matter having a functional group capable of reacting with a functional group of the water absorbent resin. An example of the organic matter is a crosslinking agent or the like. By using the organic matter, it is possible to reduce water-soluble components and further improve the granulation strength.

Further, the wording "binding" used in the present specification means to be in a state deviating from the powdery state, and an example thereof is granulation or the like.

In adding the aqueous liquid and the moisture vapor to the water absorbent resin powder, the aqueous liquid and the moisture vapor are added substantially at the same time. However, the moisture vapor is added at the same time as addition of the aqueous liquid or is added after the addition of the aqueous liquid. Alternatively, moisture vapor may be added before addition of aqueous liquid.

Further, a method of the present invention for producing particulate water absorbent resin includes the step of adding aqueous liquid and moisture vapor to water absorbent resin powder so as to bind particles of the water absorbent resin powder. Further, a method of the present invention for producing particulate water absorbent resin includes the steps of: supplying moisture vapor to water absorbent resin powder so as to bind particles of the water absorbent resin powder (integration step); and obtaining granulated water absorbent resin particles from the bound particles (particle formation step), wherein these steps are carried out at the same time. Further, it is preferable that the method of the present invention for producing particulate water absorbent resin includes plural steps of binding the particles of the water absorbent resin powder. The phrase "includes plural steps of binding the particles of the water absorbent resin powder" means to knead, by stages, (to secondarily knead) the water absorbent resin powder generated at the step of binding the particles of the water absorbent resin powder.

In the method of the present invention for binding water absorbent resin and in the method of the present invention for producing particulate water absorbent resin, a solid content of the water absorbent resin after binding the particles of the water absorbent resin powder preferably ranges from 50 to 90 wt %, more preferably from 50 to 80 wt %. Within the foregoing range, it is possible to reduce a drying time in producing particulate water absorbent resin from the water absorbent resin after binding the particles of the water absorbent resin powder. As a result, it is possible to improve the productivity of the particulate water absorbent resin.

In case where the solid content is less than 50%, it may be difficult to supply moisture to whole the water absorbent resin powder, and it may take some time to carry out the subsequent drying step, so that the energy cost may increase. This may result in an uneconomical condition. On the other hand, in case where the solid content amount exceeds 90%, it may be impossible to sufficiently integrate the water absorbent resin powder.

A moisture content of the water absorbent resin obtained after the drying step is not particularly limited, but the moisture content is preferably such that the powdery state can be kept even at a room temperature in view of property of the resultant water absorbing article. Specifically, the moisture content preferably ranges from 0.2 to 30 mass %, more preferably from 0.3 to 15 mass %, still more preferably from 0.5 to 10 mass %.

The following will detail the method of the present invention for producing particulate water absorbent resin, but the same feature is included also in the method of the present invention for binding water absorbent resin. That is, the description is applicable also to the method of the present invention for binding water absorbent resin.

In the method of the present invention for producing particulate water absorbent resin, the integration step and the particle formation step may be clearly differentiated from each other in terms of (i) how to carry out the step and (ii) a condition under which the step is carried out, or both the steps may be substantially the same in terms of (i) how to carry out the step and (ii) a condition under which the step is carried out and may be regarded as a single step. In this manner, how to carry out both the steps is not particularly limited. For example, in an embodiment in which moisture (aqueous liquid and moisture vapor) is supplied to the water absorbent resin powder while being stirred, binding of the particles of the water absorbent resin powder and formation of granulated particles may be carried out substantially at the same time (substantially at a single step). In this case, both the steps are regarded as the aforementioned single step.

<Binding Step>

At the binding step in the present invention, moisture is supplied to the water absorbent resin powder, and the moisture in a form of aqueous liquid or moisture vapor is supplied so as to bind (granulate) the particles of the water absorbent resin powder.

In the method of the present invention for producing water absorbent resin, the target water absorbent resin is a conventionally known water-swelling crosslinked polymer which is a water-swelling and substantially water-insoluble crosslinked polymer and which forms anionic, nonionic, or cationic, and substantially water-insoluble hydrogel. Note that, the "water-swelling" refers to the ability of a substance of absorbing water at a rate of, for example, at least 5 or more times, preferably 50 to 1000 times the weight of the substance in ion-exchanged water. The "substantially water-insoluble" refers to such condition that an extractable polymer content (water-soluble polymer) in the water absorbent resin ranges from 0 to 50 mass %, preferably 30 mass % or less, more preferably 25 mass % or less.

The water absorbent resin can be suitably selected from conventionally known resins in accordance with purpose of use and is not particularly limited. Examples of the water absorbent resin include one kind or include two or more kinds of: (i) crosslinked partially neutralized polyacrylic acid; (ii) a hydrolyzed starch-acrylonitrile graft polymer; (iii) a starch-acrylic graft polymer; (iv) a saponified vinyl acetate-acrylic ester copolymer; (v) hydrolyzed acrylonitrile copolymer or hydrolyzed acrylamide copolymer, or crosslinked acrylonitrile copolymer or crosslinked acrylamide copolymer; (vi) a denaturalized carboxylic crosslinked polyvinyl alcohol, (vii) a crosslinked isobutylene-maleic anhydride copolymer, (viii) and the like. Above all, it is more preferable to use the carboxylic hydrophilic crosslinked polymer. A preferable example of the hydrophilic crosslinked polymer is a partially neutralized polyacrylic acid polymer obtained by (co)polymerizing (hereinafter, referred to merely as "polymerizing") a hydrophilic unsaturated monomer made mainly of acrylic acid and/or its salt (neutralizer).

Out of acid group of the hydrophilic crosslinked polymer, it is preferable that 30 to 100 mol % is neutralized by alkali metal salt (sodium salt, potassium salt, lithium salt, and the like), ammonium salt, amine salt, and the like, and it is more preferable that 50 to 90 mol % thereof is neutralized, and it is still more preferable that 60 to 80 mol % thereof is neutralized. In neutralizing the acid group, it may be so arranged that the neutralization is carried out in advance at the stage for preparing the hydrophilic unsaturated monomer before obtaining the crosslinked polymer and polymerization reaction is initiated, or it may be so arranged that acid group of the resultant crosslinked polymer is neutralized during polymerization or after completion of polymerization reaction, or these arrangements may be adopted together. In this manner, the neutralization of acid group is not particularly limited.

Basically, the water absorbent resin powder in the present invention is substantially ungranulated water absorbent resin powder referred to as (a) water absorbent primary particles each of which cannot be broken by a certain force, e.g., by a classification operation or transport (carrying) operation. Further, the method of the present invention for producing particulate water absorbent resin is favorably applicable also to a case where the water absorbent resin powder is not the water absorbent resin primary particles unlike the aforementioned state (a), but (b) the water absorbent resin primary particles are bound particles each of which has a particle diameter smaller than a desired particle diameter of particulate water absorbent resin to be finally obtained and which are suitably granulated.

A size of each particle of the water absorbent resin powder is not particularly limited as long as the powder is in such a particulate state that the object of the present invention can be achieved. The water absorbent resin powder may include only water absorbent resin fine powder (whose particle diameter is 150 μm or less for example), or may be a mixture of the fine powder and large particles (whose particle diameter is 850 μm or less inclusive of 150 μm or less), or may be water absorbent resin from which the fine powder has been removed (the water absorbent resin has particles each of which has a particle diameter of 150 μm or more and 850 μm or less). Further, the fine powder may be fine powder having been removed from the mixture at the production steps or may be fine powder exclusively obtained by intentionally crushing the water absorbent resin or adjusting a polymerization condition of the water absorbent resin in case of increasing an absorption rate. Further, the water absorbent resin powder used in granulation of the present invention may be subjected to a surface crosslinking treatment or may be free of the surface crosslinking treatment.

Out of these kinds of water absorbent resin powder, it is preferable to use water absorbent resin fine powder. An average particle diameter of the fine powder preferably ranges from 150 to 10 μm, and preferably 70 wt % or more, more preferably 90 wt % or more of particles each of which has a particle diameter substantially 150 μm or less. Further, as a shape of a particle of the fine powder, an indefinite shape obtained by aqueous solution polymerization is more preferable than a spherical shape obtained by reversed suspension polymerization in view of the granulation strength. Further, fine powder which has not been subjected to the surface crosslinking treatment is more preferable.

The moisture vapor supplied at the binding step is saturated moisture vapor, and it is preferable to release the saturated moisture vapor in the mixing device. Specifically, it is more preferable to use saturated moisture vapor of 0.11 MPa or more (102° C. or higher), it is still more preferable to use saturated moisture vapor of 0.5 MPa or more (152° C. or higher). By supplying moisture in a form of the saturated moisture vapor, it is possible to supply the moisture to whole the water absorbent resin powder in a short time and with high efficiency, and it is possible to obtain granulated particles having high strength. In this manner, such effects can be obtained.

In the present invention, when obtaining a water absorbent resin granulated product made of plural kinds of water absorbent resin powder by mixing the water absorbent resin powder and the aqueous liquid, it is more preferable to suitably select and set a temperature of the aqueous liquid before the mixture. A temperature at which the aqueous liquid ranges from a room temperature to 100° C., more preferably from a room temperature to 70° C. Further, an upper limit of the heating temperature is not higher than a boiling point of the aqueous liquid, and the boiling point may be adjusted variously by adding salt or other solvent or changing a pressure (reduction of pressure or pressurization) or the like. Generally, the heating is carried out at 100° C. since the temperature exceeding 100° C. does not cause so great change.

The following description will specifically explain the case of carrying out the binding method.

In the binding method, it is preferable to supply moisture in a form of moisture vapor while stirring the water absorbent resin powder. Specific examples thereof include a stirring granulation process, a rolling granulation process, a compressing granulation process, a flow bed granulation process, and the like, and the binding method can be favorably carried out by any of these processes. Above all, it is more preferable to adopt the stirring granulation process in view of simplicity. In case of adopting these processes, the same device and operation condition and the like as in the conventional ones can be applied except that the moisture is allowed to be supplied in a form of aqueous liquid and moisture vapor. Note that, in the present invention, it is preferable that: the device used is equipped with a nozzle or the like for injecting aqueous liquid and moisture vapor so that aqueous liquid and moisture vapor are supplied into the device, and the device is so occlusive that moisture vapor can be smoothly supplied and its internal pressure can be adjusted. Further, aqueous liquid and moisture vapor may be sprayed in supplying them.

For example, in case of carrying out the binding method by the stirring granulation process, a continuous stirring device can be used as the stirring device, and there are a vertical type and a horizontal type. Examples of the vertical continuous stirring device include a spiral pin mixer (Pacific Machinery & Engineering Co., Ltd.), a flow jet mixer, and a Schugi granulation system (FUNKEN POWTECHS INC.), and the like. Examples of the horizontal continuous stirring device include an annular layer mixer (DRAISE WERKE), a twin-screw mixer (List), and the like. In the present invention, it is preferable to bind the particles of the water absorbent resin powder by using a rotary disk mixer. Further, in the present invention, it is preferable to bind the particles of the water absorbent resin powder by using a disk mixer equipped with vanes (radial-flow type, interflow type, mixed-flow type, axial-flow type, and the like).

A condition under which aqueous liquid and moisture vapor are injected into the device can be suitably set so as to obtain desired particulate water absorbent resin in consideration of an adoptable process, an adoptable device, and the like, and the condition is not particularly limited. However, it is preferable to inject moisture vapor with a gage pressure ranging from 0.1 to 2.0 MPa, and it is more preferable to inject moisture vapor with a gage pressure ranging from 0.1 to 1.00 MPa, and it is still more preferable to inject moisture vapor with a gage pressure ranging from 0.1 to 0.50 MPa. When the gage pressure is less than 0.1 MPa, it takes some time to bind and granulate the particles of the water absorbent resin powder, which may result in formation of granulated particles having low strength. When the gage pressure exceeds 2.0 MPa, the water absorbent resin may deteriorate. As to a steam pressure, a gage pressure is kept constant up to the vicinity of the device with the inside of the mixer free from any pressure.

With respect to 100 kg/hr of the water absorbent resin powder, an amount of the moisture vapor to be added preferably ranges from 1 to 100 kg/hr, more preferably from 7 to 30 kg/hr. The amount of the moisture vapor is within the foregoing range, the moisture vapor is dispersed in voids of the particles, thereby more firmly binding the particles. Adversely, in case where the amount of the moisture vapor is less than 1 kg/hr, the particles are less bound. On the other hand, in case where the amount of the moisture vapor is larger than 100 kg/hr, the surface of the water absorbent resin is swollen, so that the particles are hardly bound.

If the moisture is supplied in the form of the moisture vapor, it is possible to more evenly and more efficiently supply the moisture to whole the water absorbent resin powder, so that it is possible to more greatly suppress an amount of the moisture added than the case of the conventional arrangement in which liquid (water or aqueous liquid) is added. As a result, it is possible to greatly reduce the energy cost required in the subsequent drying step. In case where the amount of the moisture vapor is less than 1 part by mass, it may be impossible to sufficiently bind the particles of the water absorbent resin powder. In case where the amount of the moisture vapor exceeds 100 parts by mass, the surface of the water absorbent resin is swollen, so that it may be impossible to bind the particles, and the subsequent drying step requires a long time. As a result, the energy cost may increase, which may result in economical disadvantage.

Further, also an amount of the aqueous liquid injected into the device is not particularly limited as in the aforementioned amount. However, for example, the amount of the moisture vapor added preferably ranges from 50 to 10 parts by weight, more preferably from 50 to 20 parts by weight, still more preferably from 40 to 20 parts by weight, so that a total amount is 100 parts by weight with respect to 50 to 90 parts by weight of the water absorbent resin powder.

Also an internal temperature of the device is not particularly limited as in the aforementioned setting. However, for example, the internal temperature preferably ranges from 10 to 200° C., more preferably from 20 to 180° C., still more preferably from 50 to 150° C. When the internal temperature is lower than 10° C., the moisture vapor injected into the device is condensed, which may result in difficulty in evenly supplying the moisture to whole the water absorbent resin powder. When the internal temperature exceeds 200° C., the water absorbent resin may deteriorate. Note that, how to adjust the internal temperature of the device is not particularly limited. For example, it is possible to adopt a method in which a jacket temperature is adjusted so as to adjust the internal temperature of the device or a similar method. Note that, the step of adding the aqueous liquid and the moisture vapor to the water absorbent resin powder may be carried out at a room temperature.

Also an internal pressure of the device is not particularly limited as in the aforementioned setting. For example, it is preferable that the internal pressure is higher than a normal pressure (0.101 MPa). By making the internal pressure higher than the normal pressure, it is possible to efficiently bind the particles of the water absorbent resin powder. A degree of the pressurization is not particularly limited and can be suitably set so as to obtain the foregoing effect.

Also various kinds of mechanical process conditions and a process time etc. (for example, a shape of the stirring vane, a stirring force, a stirring rate, a stirring time, and the like in the stirring granulation process, and an average retention time and the like in the continuous type) are not particularly limited and are suitably set so as to obtain desired particulate water absorbent resin in consideration of an adoptable process and a type of an adoptable device and a similar condition.

In the present invention, it is essential to mix the aqueous liquid and the moisture vapor with the water absorbent resin powder at high speed. The phrase "mix the aqueous liquid and the moisture vapor with the water absorbent resin powder at high speed" means that it takes short time to generate the granulated water absorbent resin particles after completing the mixture of the aqueous liquid, the moisture vapor, and the water absorbent resin powder. It takes short time to generate the granulated water absorbent resin particles after the aqueous liquid and the water absorbent resin powder come into contact with each other, that is, a mixing time is short. The mixing time is preferably within three minutes, more preferably within one minute, most preferably ranges from 1 second to 60 seconds.

In case where the mixing time is long, it is difficult to evenly mix the aqueous liquid and the water absorbent resin powder, and this results in formation of a large clump, so that it is impossible to obtain the target granulated water absorbent resin particles of the present invention. Further, if the mixture is continued for a long time after completion of the mixture, the water absorbent resin may deteriorate, for example, an extractable polymer content of the water absorbent resin increases, an absorbency against pressure drops, or a similar disadvantage occurs. An essential condition under which the high speed mixture is carried out is such that the heated aqueous liquid is, in a single dose, poured into the water absorbent resin powder being stirred. That is, in case of gradually adding the aqueous liquid by spraying the aqueous liquid or in a similar manner for example, it is impossible to obtain the target granulated water absorbent resin particles of the present invention. In case of gradually adding the aqueous liquid, the water absorbent resin powder becomes a large clump or becomes kneaded while the aqueous liquid is being added, which results in deterioration of the water absorbent resin. A time taken to pour the heated aqueous liquid preferably 60 seconds or shorter, more preferably 30 seconds or shorter, most preferably 10 seconds or shorter.

Inversely, the high speed mixture for achieving the object of the present invention can be realized also by a method in which the water absorbent resin powder is poured into the heated aqueous liquid being stirred. In this case, a time taken to pour the water absorbent resin powder is preferably 60 seconds or shorter, more preferably 30 seconds or shorter, most preferably 10 seconds or shorter. Further, also by a method in which the water absorbent resin powder and the heated aqueous liquid are simultaneously mixed in a single dose, it is possible to carry out the high speed mixture for achieving the object of the present invention. In this case, a time taken to pour both these raw materials is preferably 60 seconds or shorter, more preferably 30 seconds or shorter, most preferably 10 seconds or shorter. Further, there is a case where both the raw materials are continuously poured at the same time and are mixed at high speed thereby continuously producing the granulated water absorbent resin particles of the present invention.

It is preferable, for example, that the foregoing method includes: the step (binding step) in which the aqueous liquid and the moisture vapor are supplied to the water absorbent resin powder and they are kneaded so as to obtain a hydrogel water absorbent resin; and the step (multistage kneading/formation step) in which the hydrogel product is formed into a desired shape as necessary. In the kneading step, a stirring device or the like used in the aforementioned stirring granulation process is favorably used, but the device is not particularly limited. It is possible to use conventionally known various kinds of devices which can knead the raw materials.

A condition under which aqueous liquid and moisture vapor are injected into the device can be suitably set in consideration of a kind etc. of the device, and the condition is not particularly limited.

For example, it is preferable to use a mechanical stirring mixer in kneading the raw materials. Examples of the mixer include: not only the device for carrying out the stirring granulation process; but also a turbulizer (Hosokawa Micron Corporation); Lödige mixer (Lödige); a mortar mixer (Nishinihon Shikenki); and the like. Note that, any of a batch type mixer and a continuous mixer may be used.

In the formation step, the hydrogel resultant is extruded, compressed, or subjected to a similar treatment so as to be in a desired shape, and the step can be carried out as necessary. In terms of the extrusion, the compression, and a treatment condition at this time, conventionally known device and technique and condition can be adopted. The device may be integrated to the aforementioned stirring device or the like used in the kneading step. Note that, not only the formation by the extruder but also conventionally known various kinds of resin formation processes such as formation by flowing the raw materials into a container having a predetermined shape can be adopted. For example, it is possible to adopt a method using a compacting machine, a briquetting roll, a tableting machine, or the like.

In the formation step, it is possible to form the raw materials into various shapes such as a sheet shape, a plate shape, a clumpy shape, a strand shape, and the like.

In the drying step, a drying treatment is carried out so as to adjust moisture contained in the hydrogel resultant after the kneading step or after the formation step. The drying step is required particularly in case of crushing the resultant subsequently.

In case where the bound particles of the water absorbent resin powder are obtained by carrying out the binding step, as described above, the particle formation step is carried out at the same time as the integration step, so that the same explanation as in the foregoing explanation is applicable herein. Thus, as to the various kinds of devices, process conditions, and the like that were explained above, it is more preferable to suitably select and set them also in consideration of a desired particle diameter of the particulate water absorbent resin.

In case where the bound particles of the water absorbent resin powder are obtained by carrying out the multistage kneading/formation step, for example, it is preferable that the method further includes: the step (finely cutting step) in which the bound resultant is cut into pieces each of which has an appropriate size; and the step (crushing step) in which the bound resultant is crushed into pieces each of which has a desired particle diameter.

In the finely cutting step, the bound resultant of the water absorbent resin powder is finely cut into pieces each of which has a size capable of being subjected to the crushing step or a size making it easier to carry out the crushing step. The finely cutting step is carried out as necessary.

The finely cutting means is not particularly limited, and ordinary finely cutting means or fragmentation means such as scissors, a cutter, a cutter mill, a guillotine cutter, a meat chopper, a slitter, a rotary cutter, and the like are adoptable.

Although the finely cutting step varies depending on the finely cutting means, as described above, it may be easier to carry out the finely cutting step with the water absorbent resin powder layer or the hydrogel product before being subjected to the drying step.

A size of each piece obtained by finely cutting the raw material, that is, a size and shape each piece obtained by finely cutting the raw material varies depending on not only a kind of the crushing device but also conditions such as purpose of use, required performance, a type of the finely cutting means, and a similar condition. For example, it is possible to obtain a fine lath shape, a polygonal shape, a disk shape, a cylindrical shape, a prism shape, an indefinite shape, and the like.

When a maximum size of a diameter of each of variously shaped pieces obtained by finely cutting the bound product is defined as a maximum length of each piece obtained by finely cutting the bound product, it is preferable to carry out the finely cutting step so that the maximum length ranges from 0.5 to 40 mm, preferably from 1 to 5 mm.

In the crushing step, the bound product obtained in the binding step and the multistage kneading/formation step or the bound product obtained in the finely cutting step is crushed into particulate water absorbent resin including particles each of which has a desired particle diameter. Any one of both the bound products can be crushed depending on a kind and a characteristic of the crushing device.

In crushing the bound product, also a crushing device and a crushing method used in conventionally known various resin production techniques can be adopted.

It is difficult to carry out the crushing step with respect to the bound product containing a large amount of moisture, so that it is preferable to carry out the crushing step with respect to the bound product having been subjected to the drying step.

A particle diameter of the granulate particles obtained in the binding step can be suitably set in consideration of purpose of use of the particulate water absorbent resin. For example, the particle diameter preferably ranges from 100 μm to 40 mm, more preferably from 150 μm to 5 mm, still more preferably from 150 μm to 1 mm. When the particle diameter is less than 100 μm, the granulated particles are broken, so that the broken particles may become water absorbent resin primary particles. When the particle diameter exceeds 40 mm, the water absorbent resin may remain undried after carrying out the drying step. Particularly, for purpose of use as a sanitary material such as a disposable diaper or napkin, a mass average particle diameter preferably ranges from 100 μm to 1 mm, more preferably from 150 to 800 μm. For purpose of use as a water retaining agent or the like in agriculture or horticulture, the mass average particle diameter preferably ranges from 500 μm to 5 mm.

It is preferable to crosslink, as described below, a vicinity of a surface of each of pieces obtained by crushing and classifying the water absorbent resin bound and dried particles obtained in the foregoing manner. That is, it is preferable that: the water absorbent resin powder is formed into the water absorbent resin bound particles in accordance with the binding method of the present invention, and the water absorbent resin bound particles are dried so as to have a mass average particle diameter of 100 μm to 1 mm, and a water absorbent resin obtained in this manner which has a less amount of fine powder is surface-crosslinked, thereby obtaining a water absorbing agent.

A shape of the resultant bound particles varies depending on not only a type of the mixing device but also a mixing process and a condition thereof. For example, it is possible to obtain a spherical shape, a disk shape, a polygonal shape, an indefinite shape, a clumpy shape (spherical shape, disk shape, polygonal shape, rod shape) and the like.

The bound particles formed in the binding step are granulated particles. This can be confirmed by finding, with an optical microscope, (i) such fact that a plurality of particles are gathered and clumped with each particle keeping its shape and (ii) such fact that the particles are swollen as a plurality of discontinuous particles in absorbing liquid.

In the method of the present invention for producing particulate water absorbent resin, the granulated particles may be such that a surface of each particle is crosslinked. This is preferable since it is possible to improve the particulate water absorbent resin's various properties such as an absorbency against pressure and similar properties. In case of the granulated particles each of which has a crosslinked surface, it is preferable to carry out the surface crosslinking treatment with respect to the granulated particles obtained in the binding step. Also in case of using the surface-crosslinked powder as the water absorbent resin powder as described above, the surface of each granulated particle is naturally crosslinked, so that also such arrangement is preferable. Note that, the surface crosslinking treatment will be detailed in the below description of the surface modification step.

It is preferable, for example, that the method of the present invention for producing particulate water absorbent resin includes: not only the binding step and the multistage kneading/formation step; but also general water absorbent resin production steps, i.e., a step of synthesizing a polymer serving as the water absorbent resin (polymerization step); a step of drying the polymer (polymer drying step); and a step of essentially classifying the dried particles so as to have a desired particle diameter (polymer classification step), wherein the water absorbent resin powder used in the binding step is water absorbent resin fine particles removed in the polymer classification step.

Further, it is more preferable that the method includes a surface modification step, a transport step, and a storage step.

The various steps are described as follows.

<Polymerization Step>

In the present invention, the water absorbent resin contains acid group and/or its salt (neutralized product). Thus, it is preferable that the water absorbent resin is obtained by polymerizing a hydrophilic unsaturated monomer containing an acid-group-containing unsaturated monomer as a main component. Note that, examples of the acid-group-containing unsaturated monomer include also a monomer which becomes acid group through hydrolysis after the polymerization (acrylonitrile for example), but it is preferable to use an acid-group-containing unsaturated monomer which contains acid group at the time of polymerization. As the hydrophilic unsaturated monomer which contains the acid-group-containing unsaturated monomer, it is more preferable to use a hydrophilic unsaturated monomer containing acrylic acid and/or its salt (neutralized product) as a main component.

In case where the hydrophilic unsaturated monomer contains acrylic acid and/or its salt (neutralized product) as a main component, an unsaturated monomer other than acrylic acid and/or its salt (neutralized product) can be used as necessary (hereinafter, this monomer will be referred to as "other monomer"). Specific examples of the other monomer include: anionic unsaturated monomer such as methacrylic acid, maleic acid, vinyl sulfonic acid, styrene sulfonic acid, 2-(meth)acrylamide-2-methylpropane sulfonic acid, 2-(meth)acryloyl ethane sulfonic acid, 2-(meth)acryloyl propane sulfonic acid, and salt thereof; nonionic hydrophilic unsaturated monomer such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl(meth)acrylate, 2-hydroxypropyl (meth)acrylate, methoxypolyethyleneglycol(meth)acrylate, polyethyleneglycolmono(meth)acrylate, vinylpyridine, N-vinylpyrrolidone, N-acryloylpiperidine, and N-acryloylpyrrolidine; cationic unsaturated monomer such as N,N-dimethylaminoethyl(meth)acrylate, N,N-diethylaminoethyl (meth)acrylate, N,N-dimethylaminopropyl(meth)acrylate, N,N-dimethylaminopropyl(meth)acrylamide and quaternary salt thereof; and the like. However, the other monomer is not particularly limited. An amount of the other monomer is preferably 30 mol % or less, more preferably 10 mol % or less, relative to the whole hydrophilic unsaturated monomer.

It is preferable that the water absorbent resin obtained by polymerizing the hydrophilic unsaturated monomer contains carboxyl group. An amount of the carboxyl group of the water absorbent resin is not particularly limited, but it is preferable that an equivalent of the carboxyl group is 0.01 or more with respect to 100 g of the water absorbent resin.

A method for obtaining the water absorbent resin by polymerizing the hydrophilic unsaturated monomer, specifically, a method for obtaining a hydrogel polymer of the water absorbent resin by polymerizing the hydrophilic unsaturated monomer is not particularly limited, but it is possible to adopt conventionally known methods such as aqueous solution polymerization, reversed phase suspension polymerization, bulk polymerization, precipitation polymerization, and the like. Above all, due to the easiness to control the polymerization reaction and favorable properties (absorbent property or the like of the swollen gel for example) of the resultant water absorbent resin, it is preferable to adopt a method in which an aqueous solution of the hydrophilic unsaturated monomer is polymerized, i.e., it is preferable to adopt the aqueous solution polymerization and the reversed suspension polymerization, and it is particularly preferable to adopt the aqueous solution polymerization.

The reversed suspension polymerization is a method in which monomer aqueous solution is suspended in a hydrophobic organic solvent so as to be polymerized. Such polymerization method is described for example in U.S. Pat. No. 4,093,776, U.S. Pat. No. 4,367,323, U.S. Pat. No. 4,446,261, U.S. Pat. No. 4,683,274, and U.S. Pat. No. 5,244,735. The hydrophilic monomer, the polymerization initiator, and the like exemplified in each of these methods can be applied to the present invention.

The aqueous solution polymerization is a method in which monomer aqueous solution is polymerized without using a dispersion solvent. Such polymerization method is described for example in U.S. Pat. No. 4,625,001, U.S. Pat. No. 4,873, 299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, and U.S. Pat. No. 5,380,808, and European Patent No. 0811636, European Patent No. 0955086, and European Patent No. 0922717. The hydrophilic monomer, the polymerization initiator, and the like exemplified in each of these polymerization methods can be applied to the present invention. Further, the method of the aqueous solution polymerization is not particularly limited. However, favorable examples thereof include: a method in which the monomer aqueous solution is polymerized while crushing the resultant hydrogel crosslinked polymer in a single-screw or double-arm kneader (kneader polymerization); a method in which the monomer aqueous solution is supplied into a predetermined container or onto a driving belt and a gel obtained by polymerization is crushed by a meat chopper or the like (belt polymerization); and a similar method.

In the polymerization method, a concentration of the hydrophilic unsaturated monomer in the aqueous solution of the hydrophilic unsaturated monomer (hereinafter, the aqueous solution is referred to as "monomer aqueous solution") is determined according to a temperature of the aqueous solution and a kind of the monomer and is not particularly limited, but is preferably 10 mass % or more, more preferably ranges from 10 to 65 mass %, still more preferably from 10 to 50 mass %, particularly preferably from to 40 mass %. In the polymerization method, when preparing the monomer aqueous solution, a solvent other than water may be used together as necessary, and a kind of the solvent used together is not particularly limited.

In polymerizing the hydrophilic unsaturated monomer, it is possible to use: a radical polymerization initiator such as potassium persulfate, sodium persulfate, ammonium persulfate, t-butylhydroperoxide, hydrogen peroxide, 2,2'-azobis (2-amidino-propane) dihydrochloride; radical photopolymerization initiator such as 2-hydroxy-2-methyl-1-phenyl-propane-1-one; or an active energy ray such as an ultraviolet ray and an electron ray. Further, in case of using a radical polymerization initiator, redox polymerization may be carried out by using a reducer such as sodium sulfite, sodium bisulfite, ferrous sulfate, L-ascorbic acid, and the like, together. An amount of polymerization initiators used is preferably 0.001 mol % or more and 2 mol % or less, more preferably 0.01 mol % or more and 0.5 mol % or less, relative to the whole monomer. Further, the polymerization reaction may be initiated by irradiating an active energy ray such as a radial ray, an electron ray, and an ultraviolet ray to the reaction system or may be initiated by using the aforementioned polymerization initiator together.

A reaction temperature in the polymerization method is not particularly limited, but preferably ranges from 15 to 130° C., more preferably from 20 to 120° C. Further, various reaction conditions such as a reaction time, a polymerization pressure, and the like are not particularly limited and may be suitably set according to kinds and compositions of the monomer and the polymerization initiator, a reaction temperature, and the like.

In obtaining the water absorbent resin of the present invention, it is preferable to introduce a crosslinked structure into the resultant water absorbent resin. The internal crosslinked structure may be formed by using a self-crosslinking hydrophilic unsaturated monomer without particularly using any internal crosslinking agent or may be formed by using, as the internal crosslinking agent, a compound having in its single molecule two or more reactive groups (substituents) each of which is reactable with polymerizable unsaturated group and/or carboxyl group. Both the processes are preferable, but it is more preferable to adopt the latter process in which the internal crosslinking agent is used.

Examples of the internal crosslinking agent include: N,N'-methylenebis(meth)acrylamide, (poly)ethyleneglycol di(meth)acrylate, (poly)propyleneglycol di(meth)acrylate, trimethylolpropanetri(meth)acrylate, trimethylolpropanedi(meth)acrylate, glycerintri(meth)acrylate, glycerinacrylate-methacrylate, ethylene oxide denatured trimethylolpropanetri(meth)acrylate, pentaerythritoltetra(meth)acrylate, dipentaerythritolhexa(meth)acrylate, triallyl cyanurate, triallyl isocyanurate, triallyl phosphate, triallyl amine, poly (meth)allyloxyalkane, (poly)ethyleneglycoldiglycidylether, glyceroldiglycidylether, ethyleneglycol, polyethyleneglycol, propyleneglycol, glycerin, pentaerythritol, ethylenediamine, polethyleneimine, glycidyl(meth)acrylate, and the like, and the internal crosslinking agent is not particularly limited. These internal crosslinking agents may be used solely or may be used in a combination of two or more kinds. Further, out of the above-mentioned internal crosslinking agents, an internal crosslinking agent having polymerizable unsaturated group in its molecule is used, thereby further improving an absorbent property or the like of the resultant water absorbent resin.

In case of introducing the crosslinked structure into the polymer by using the internal crosslinking agent, the internal crosslinking agent may be added to the reaction system in a single dose or in plural doses. Further, the internal crosslinking agent is added to the reaction system before, during, or after the polymerization of the hydrophilic unsaturated monomer or is added after neutralization.

With respect to the hydrophilic unsaturated monomer, an amount of the internal crosslinking agent preferably ranges from 0.005 to 3 mol %, more preferably from 0.01 to 1.5 mol %. In case where the amount of the internal crosslinking agent is less than 0.005 mol % and in case where the amount of the internal crosslinking agent is more than 3 mol %, it may be impossible to obtain the water absorbent resin having the desired water absorbent property.

In obtaining the water absorbent resin by polymerizing the hydrophilic unsaturated monomer, it is possible to add hydrophilic polymers such as starch, a derivative of starch, cellulose, a derivative of cellulose, polyvinyl alcohol, polyacrylic acid (salt), cross-linked polyacrylic acid (salt), and the like or it is possible to add a chain transfer agent such as hypophosphorous acid (salt) or it is possible to add a water-soluble or water-dispersion surfactant or the like.

<Polymer Drying Step>

The polymer obtained by the polymerization method, that is, the hydrogel polymer of the water absorbent resin is dried so that its solid content is adjusted, thereby obtaining the water absorbent resin having the desired moisture content.

In view of reduction of coloring and reduction of residual monomer, the drying operation is initiated (the polymer is placed into the dryer) preferably within 2 hours, more preferably within 1 hour, still more preferably within 0.5 hours, particularly preferably within 0.2 hours from completion of the polymerization (after being discharged from the polymerization device).

In the drying operation, a general hot air dryer or a general heating oven can be used. Examples thereof include a groove stirring dryer, a rotation dryer, a disk dryer, a fluidized-bed dryer, a flash dryer, an infrared dryer, and the like. A drying temperature preferably ranges from 40 to 250° C., more preferably from 90 to 200° C., still more preferably from 120 to 180° C. A drying time depends on a surface area size and a moisture content of the polymer and on a type of the dryer and is set so as to have a desired moisture content, but it is preferable to carry out the hot air drying for 0.1 to 5 hours.

The moisture content of the water absorbent resin obtained after the drying operation is not particularly limited. However, in view of properties of the resultant water absorbent resin product, it is preferable to keep a powdery state showing fluidity even at room temperature. Specifically, the moisture content preferably ranges from 0.2 to 30 mass %, more preferably from 0.3 to 15 mass %, still more preferably from 0.5 to 10 mass %.

<Polymer Classification Step>

The dried water absorbent resin obtained in the polymer drying step is subjected to a step in which classification is essentially carried out so as to have a desired particle diameter, thereby adjusting the particle diameter corresponding to the purpose of use.

The dried water absorbent resin may be capable of being classified as particulate water absorbent resin without any modification, but a step of pulverizing or segmenting the dried water absorbent resin by using a pulverizer or the like (polymer pulverizing step) is further carried out as necessary so as to form the particulate water absorbent resin, and then the particulate water absorbent resin is classified.

Examples of the pulverizer used in the polymer pulverizing step include a roller mill, a knife mill, a hummer mill, a pin mill, a jet mill, and the like. It is preferable that the pulverizer includes means for heating an internal wall surface of the pulverizer itself.

A shape of each piece of the particulate water absorbent resin having been obtained by pulverizing or segmenting is not particularly limited, and the shape may be any one of a spherical shape, a scaly shape, an indefinitely-pulverized shape, a fibrous shape, a granular shape, a rod shape, an oblate shape, and the like.

In case where the polymer pulverization step is carried out, the classification is carried out preferably after the polymer pulverization step and before a below-described surface modification step. It is more preferable that the surface modification step includes second classification.

A particle diameter (particle size) of the classified water absorbent resin (final product) is preferably 2 mm or less, more preferably ranges from 10 μm to 1 mm. A mass average particle diameter varies depending on purpose of use, but generally, the mass average particle diameter preferably ranges from 100 μm to 1 mm, more preferably from 150 to 800 μm, still more preferably from 200 to 700 μm, particularly preferably from 300 to 600 μm.

It is preferable that the classified water absorbent resin also includes 95 to 100 mass % of particles whose particle diameter ranges from 850 to 150 μm (particles which pass through a standard sieve whose mesh size is 850 μm and which do not pass through a standard sieve whose mesh size is 150 μm: a JIS standard sieve or a similar sieve is used). In this case, it is more preferable that the classified water absorbent resin includes a less amount of particles whose particle diameter is, for example, preferably less than 100 μm, more preferably less than 150 μm. Specifically, the amount of the particles is preferably less than 15 mass %, more preferably less than 10 mass %, still more preferably less than 5 mass %, particularly preferably less than 3 mass %, most preferably less than 1 mass %. Further, it is more preferable that the classified water absorbent resin includes a less amount of coarse particles (substantially, particles whose particle diameter is preferably 1000 μm or more, more preferably 850 μm or more, for example). Specifically, the amount of the particles is preferably 5 mass % or less, more preferably 1 mass % or less.

In the present invention, as described above, it is preferable to use the water absorbent resin fine particles, having been removed in the polymer classification step, as the water absorbent resin powder in the integration step. The water absorbent resin fine particles, having been removed in general water absorbent resin production steps (i.e., water absorbent resin particles having been removed and regarded as being unnecessary) can be easily reused as particulate water absorbent resin having a desired particle diameter and the like, thereby improving the productivity and the like in the entire production steps. Further, in this case, when the water absorbent resin fine particles having been removed include water absorbent resin fine particles whose particle diameter is less than 150 μm, it is more significant to carry out the foregoing arrangement, and this results in more remarkable effect for enhancing the productivity to a level which cannot be realized conventionally. Thus, the foregoing setting is preferable. It is more preferable that water absorbent resin fine particles whose particle diameter is less than 105 μm are included. Further, preferably 50 mass %, more preferably 80 mass % of the water absorbent resin fine particles whose particle diameter is equal to or less than the predetermined particle diameter are included.

<Surface Modification Step>

Examples of the surface modification carried out with respect to the water absorbent resin include: (i) surface crosslinking carried out with a surface crosslinking agent; (ii) surface coating carried out with water-insoluble fine particles; (iii) surface coating carried out with a surfactant; (iv) surface coating carried out with hydrophilic or hydrophobic polymer; (v) surface coating carried out with an antibacterial agent or a deodorant; (vi) surface coating carried out with hydrophilic or hydrophobic organic compound; and the like. These surface modification treatments may be adopted solely or may be adopted in a combination of two or more kinds. However, it is preferable to adopt (i) the surface crosslinking carried out with a surface crosslinking agent and/or (ii) the surface coating carried out with water-insoluble fine particles, and it is more preferable to adopt a combination of both the treatments (i) and (ii).

Further, the surface modification step may be carried out before or after the classification carried out in the polymer classification step. In this manner, the timing of the surface modification step is not particularly limited. In case where the surface modification step is carried out before the classification, the water absorbent resin powder removed in the classification has been subjected to the surface modification treatment (surface crosslinking treatment for example). In case where the surface modification step is carried out after the classification, it is also possible to remove the powder by further carrying out the classification step after the surface modification step.

In consideration of properties of the resultant water absorbent resin, an amount of the surface modification agent (surface crosslinking agent, water-insoluble fine particles, and the like) preferably ranges from 0.001 to 10 parts by mass, more preferably from 0.01 to 8 parts by mass, still more preferably from 0.05 to 5 parts by mass, most preferably from 0.1 to 2 parts by mass, with respect to 100 parts by mass of the water absorbent resin.

The surface crosslinking treatment is a treatment for improving properties by enhancing a crosslinking density in the vicinity of the surface of the water absorbent resin from the inside of the particles, wherein each of various kinds of surface crosslinking agents (second crosslinking agent used in addition to the internal crosslinking agent) is added to the water absorbent resin so as to crosslink only the surface.

The surface crosslinking agent is not particularly limited, but it is preferable to use a crosslinking agent reactive with carboxyl group, above all, it is preferable to use a dehydration reactive crosslinking agent since this crosslinking agent allows for formation of water absorbent resin having excellent properties. Note that, the "dehydration reactive" means that functional group (particularly, functional group in the vicinity of the surface) of the water absorbent resin has a dehydration reaction with the crosslinking agent, preferably, dehydration esterification and/or dehydration amidation is carried out, more preferably dehydration esterification is carried out.

In case where the water absorbent resin contains carboxyl group for example, examples of the dehydration reaction crosslinking agent include: a crosslinking agent containing hydroxyl group such as polyvalent alcohol; a crosslinking agent containing amino group such as polyvalent amine; cyclic crosslinking agent such as alkylenecarbonate or mono, di, or poly oxazolidinone compound and oxetane compound, e.g., 3-methyl-3-oxetanemethanol and the like, wherein a ring open reaction of the cyclic crosslinking agent causes formation of hydroxyl group or amino group, and the hydroxy group or the amino group causes a crosslinking reaction; and a similar crosslinking agent. Specific examples thereof include: polyvalent alcohol compounds such as propyleneglycol, 1,3-propanediol, 2-methyl-1,3-propanediol, glycerin, 1,4-butandiol, and 1,5-pentandiol; alkylene carbonate compounds such as 1,3-dioxolane-2-one, 4-methyl-1,3-dioxolane-2-one; oxetane compounds and polyvalent oxetane compounds such as 3-methyl-3-oxetanemethanol; and the like. Above all, it is preferable to use one or more kinds of the dehydration reaction crosslinking agent selected from polyvalent alcohol, alkylenecarbonate, oxazolidinone compound, and (polyvalent)oxetane compound, and it is more preferable to essentially use polyvalent alcohol.

Examples of the surface crosslinking agent include not only the dehydration reaction crosslinking agents but also: epoxy compounds such as ethylene glycol diglycidyl ether and γ-glycidoxypropyltrimethoxysilane; polyvalent isocyanate compounds such as 2,4-tolylene diisocyanate; polyvalent oxazoline compounds such as 1,2-ethylenebisoxazoline; silane coupling agents such as γ-aminopropyltrimethoxysilane; polyvalent aziridine compounds such as 2,2-bishydroxymethylbutanol-tris[3-(1-aziridinyl)propionate]; and non-dehydrating crosslinking agents of polyvalent metals such as beryllium, magnesium, calcium, strontium, zinc, aluminum, iron, chromium, manganese, titan, and zirconium.

The surface crosslinking agent may be mixed with the water absorbent resin using water and/or a hydrophilic organic solvent.

The amount of water used as a solvent is preferably 0.1 to 10 parts by mass, more preferably 0.5 to 8 parts by mass, and most preferably 1 to 5 parts by mass, all with respect to 100 parts by mass of the water absorbent resin.

Examples of the hydrophilic organic solvent include: alcohols such as ethyl alcohol, propyl alcohol, and isopropyl alcohol; ketones such as acetone; ethers such as dioxane, alkoxy(poly)ethyleneglycol, and tetrahydrofuran; amides such as ε-caprolactam; and sulfoxides such as dimethylsulfoxide. The amount of hydrophilic organic solvent used is preferably within a range of 0 to 10 parts by mass, more preferably 0 to 5 parts by mass, and most preferably 0 to 3 parts by mass, all with respect to 100 parts by mass of the water absorbent resin.

The method of mixing the surface crosslinking agent is not limited to a particular method. For example, the surface crosslinking agent in water, a hydrophilic organic solvent, inorganic powder, and the like may be mixed with the water absorbent resin in separate doses or in a single dose. It is, however, more preferable that the surface crosslinking agent is first mixed with all these solvent components, and then the resultant mixture is added to the water absorbent resin in the form of an aqueous solution.

At the time of the mixture, water-insoluble fine particles or a surfactant may coexist as long as an amount thereof ranges from 0 to 10 parts by mass (with respect to the water absorbent resin) for example.

Among these different mixing methods, it is preferable that the surface crosslinking agent optionally dissolved in water and/or hydrophilic organic solvent is mixed dropwise with the water absorbent resin. More preferably, the surface crosslinking agent optionally dissolved in water and/or hydrophilic organic solvent is sprayed into the water absorbent resin. A size (diameter) of the sprayed droplet is preferably not more than 300 μm, and more preferably not more than 200 μm. The temperature of the solution to be sprayed is preferably in a range of 0° C. to the boiling point of the solution, more preferably 5 to 50° C., and most preferably 10 to 30° C., taking into consideration ease of mixing and stability. The temperature of the water absorbent resin powder before mixing is preferably in a range of 0 to 80° C., and more preferably 40 to 70° C., taking into consideration ease of mixing.

The type of mixer used in mixing is not particularly limited as long as it can generate power that is strong enough to attain uniform mixing. Examples of such a mixer include a cylindrical mixer, double-wall cone-shaped mixer, high-speed stirring mixer, wedge-shaped mixer, ribbon mixer, screw mixer, fluidized furnace rotary disk mixer, air mixer, double-arm kneader, inner mixer, pulverizing kneader, rotary mixer, and screw extruder. Specifically, it is preferable to carry out the mixture by the high-speed stirring mixer within 3 minutes.

When heating is carried out in the surface crosslinking treatment, heating is carried out preferably for 1 to 180 minutes, more preferably 3 to 120 minutes, and most preferably 5 to 100 minutes. The heating temperature (defined by the temperature of a heated medium or material) is preferably in a range of 100 to 250° C., more preferably 140 to 220° C., further preferably 150 to 230° C., and most preferably 160 to 220° C. The heating may be carried out using a common dryer or furnace, examples of which include a trenched mixing dryer, rotary dryer, disk dryer, fluidized bed dryer, air dryer, and infrared dryer.

At this time, additives such as an inactive surfactant, inactive deodorant, and inactive inorganic fine particles may be added with or without introduction of surface-crosslinkage. Here, "inactive" means that the additives are substantially non-reactive to the water absorbent resin.

Note that, these surface crosslinking methods are described in European Patent No. 0349240, European Patent No. 0605150, European Patent No. 0450923, European Patent No. 0812873, European Patent No. 0450924, European Patent No. 0668080, U.S. Pat. No. 5,409,771, U.S. Pat. No. 5,597,873, U.S. Pat. No. 5,385,983, U.S. Pat. No. 5,610,220, U.S. Pat. No. 5,633,316, U.S. Pat. No. 5,674,633, U.S. Pat. No. 5,462,972, International Publication No. WO99/42494, International Publication No. WO99/43720, International Publication No. WO99/42496, and the like. These surface crosslinking methods are applicable also to the present invention.

A cationic polymer compound used as an additive for the surface modification of the water absorbent resin is added to improve properties of the water absorbent resin, for example, such as ease of anchoring to a sanitary article. A mass average molecular weight of the cationic polymer compound is preferably not less than 2000, more preferably not less than 5000, and most preferably not less than 10000. An amount of the cationic polymer compound preferably ranges from 0.01 to 10 parts by mass, more preferably from 0.05 to 5 parts by mass, still more preferably from 0.1 to 3 parts by mass, with respect to 100 parts by mass of the water absorbent resin. The cationic polymer compound is added either directly or in the form of a solution (aqueous solution). Preferable examples of the cationic polymer compound are polyethyleneimine, polyvinylamine, polyarylamine, a condensate of polyamidoamine and epichlorohydrin, polyamidine, a partial hydrolysate of poly(N-vinylformaldehyde), and salts of these compounds.

With the use of water-insoluble fine particles as an additive for the surface modification, it possible to improve permeability of the water absorbent resin, and blocking resistance of the water absorbent resin when it has absorbed moisture. As the water-insoluble fine particles, organic or inorganic water-insoluble fine particles may be adopted with a particle size of preferably not more than 10 µm in diameter, more preferably not more than 1 µm in diameter, and most preferably not more than 0.1 µm in diameter (the diameter of the particles is measured by using a coulter counter, for example). More specifically, silicon oxide (product name: Aerosil made by Nippon Aerosil Co., Ltd.), titanium oxide, or aluminum oxide may be used as the water-insoluble fine particles. Mixing is carried out by a method such as dry-blending or slurry blending. An amount of the fine particles is preferably not more than 10 parts by mass, more preferably ranges from 0.001 to 5 parts by mass, still more preferably from 0.01 to 2 parts by mass, with respect to 100 parts by mass of the water absorbent resin.

In addition to the surface crosslinking agent in the surface modification step, other additives (denoted as "other additives" hereinafter) may be added as required. Examples of such other additives include: deodorant agents; antibacterial agents; fragrant material; foaming agents; pigment; dye; hydrophilic staple fibers; plasticizers; adhesives; surfactants; fertilizer; oxidants; reductants; water; salt; chelators; disinfectants; hydrophilic polymers such as polyethylene glycol and polyethylene imine; hydrophobic polymers such as paraffin; thermo-plastic resins such as polyethylene and polypropylene; and thermo-setting resins such as polyester resin and urea resin. These additives may be added in an adding step to impart various functions to the water absorbent resin. Preferably, these additives are added to the surface of the water absorbent resin in the adding step. These additives are used in an amount of generally 0 to 30 parts by mass, preferably 0 to 10 parts by mass, and more preferably 0 to 1 parts by mass, all with respect to 100 parts by mass of the water absorbent resin. Note that, in the present invention, also the surface crosslinking agent and the additive are generically referred to as "water absorbent resin" as long as the water absorbent resin serves as a main component and the surface crosslinking agent and/or the additive are substantially integrated to the water absorbent resin after the surface crosslinking treatment is carried out with respect to the water absorbent resin and/or after adding the additive to the water absorbent resin.

In the water absorbent resin obtained by carrying out the surface crosslinking treatment or the internal crosslinking treatment, an amount of an uncrosslinked polymer, i.e., an extractable component content preferably preferably ranges from 0 to 50 mass %, more preferably not more than 30 mass %, still more preferably not more than 25 mass %.

A favorable example of the method of the present invention for producing particulate water absorbent resin is such that: the granulated particles obtained by carrying out the binding step with respect to the water absorbent resin powder having removed by the classification in the polymer classification step of general water absorbent resin production steps are added in the polymer classification step (specifically, at the time of classification in the polymer classification step) or in the previous step so as to be reused in case where the granulated particles are subjected to the drying treatment, and the granulated particles obtained by carrying out the binding step with respect to the water absorbent resin powder having removed by the classification in the polymer classification step of general water absorbent resin production steps are added previous to the polymer classification step so as to be reused in case where the granulated particles are not subjected to the drying treatment. Herein, in case where the granulated particles are not subjected to the drying treatment, it is preferable to reuse the granulated particles in the polymer drying step pervious to the polymer classification step or in a further previous step, and this is applicable also to the following description. Note that, an example of the case where the granulated particles are not subjected to the drying treatment is the case where the binding step is carried out or a similar case.

The granulated particles may be added in any step as long as the step is previous to the polymer classification step of the general water absorbent resin production method. Above all, more preferably, the granulated particles are added to a monomer preparation liquid in the polymerization step, or the granulated particles are added to a polymer (hydrogel polymer) obtained after the polymerization step, classification is carried out in addition to the polymer classification step (or the granulated particles are added in the polymer classification step so as to be dried and classified or subjected to a similar treatment).

In this manner, the water absorbent resin powder having been removed in the general water absorbent resin production method are returned to the previous production step, thereby greatly improving the yield in producing the water absorbent resin product.

In the granulated particles obtained by the conventional granulation method, that is, by the method in which water or aqueous liquid is added to the water absorbent resin powder and granulation is carried out, a large amount of powder which has not been granulated remains as described above. Thus, even if the powder is reused as described above, it is impossible to avoid the same problem as in the conventional case of reusing powder without any modification.

In reusing the granulated particles by adding to the monomer preparation liquid or the hydrogel polymer, the water absorbent resin powder having been subjected to classification or a similar treatment is conventionally added without any modification. In this case, there occur the following problems: fish eyes occur in the monomer preparation liquid, so that it is impossible to evenly disperse and dissolve the granulated particles; the water absorbent resin powder absorbs moisture or moisture vapor emitted from the hydrogel polymer, so that the powder adheres to a wall face in the vicinity of the inlet. Thus, as described above, the water absorbent resin powder having been subjected to classification is formed into granulated particles and the granulated particles are added to the monomer preparation liquid or the hydrogel polymer, thereby entirely and effectively solving the conventional problems.

In reusing the granulated particles by adding in the polymer classification step, it is preferable to reuse the granulated particles each having the desired particle diameter in consideration of purpose of use or the like of the resultant particulate water absorbent resin. This makes it possible to efficiently reuse the water absorbent resin powder, having been removed from the production steps, as new particulate water absorbent resin having a desired particle diameter.

A concentration of the hydrogel polymer ranges from 40 to 90%, preferably from 50 to 80%. A difference between the monomer preparation liquid of the acid-group-containing unsaturated monomer or the hydrogel polymer and the granulated particles in terms of a solid component concentration is preferably 50 wt % or less, more preferably 0 to 30 wt %, most preferably 0 to 10 wt %. In case where the difference in terms of the solid component concentration is large, monomer polymerization is carried out excessively or delays or similar disadvantage occurs in adding the granulated particles to the monomer preparation liquid, and the drying operation is carried out unevenly in adding the granulated particles to the hydrogel polymer.

In this manner, the method according to the present invention for producing particulate water absorbent resin is, for example, a method in which aqueous liquid is supplied to water absorbent resin powder so as to bind and granulate the powder, and a specific arrangement thereof is not particularly limited as long as aqueous liquid and moisture vapor are used together.

Further, the method according to the present invention for producing particulate water absorbent resin may be arranged, for example, so as to include a step of continuously binding and granulating the water absorbent resin powder.

Further, the method according to the present invention for producing particulate water absorbent resin may be arranged, for example, so that 50 to 90 parts by weight of the water absorbent resin powder and 50 to 10 parts by weight of the aqueous liquid are stirred and mixed.

Further, the method according to the present invention for producing particulate water absorbent resin may be arranged, for example, so that an amount of the moisture vapor ranges from 1 to 100 kg/hr with respect to 100 kg/hr of the water absorbent resin powder.

EXAMPLES

The present invention is more specifically described below with the following Examples and Comparative Examples. The present invention is however not limited to those examples. Note that, for ease of explanation, the "parts by mass" may be expressed simply as "parts", and "litter" may be expressed simply as "L". Similarly, "mass %" may be expressed as "wt %", and "particulate water absorbent resin" may be expressed as "water absorbent resin particles".

[Method for Measuring Properties of Water Absorbent Resin Particles]

<Moisture Content>

The measurement of moisture content was carried out as follows. 1 g of the sample such as granulated (bound) water absorbent resin particles was taken to an aluminum cup (bottom diameter is 52 mm and height is 22 mm) and dried for 3 hours by being laid still in a homothermal dryer (NDO-450 produced by Tokyo Rika Kiki Co., Ltd.) at 180° C. A mass before being dried and a mass after being dried were measured, and the moisture content (%) was calculated in accordance with the following expression.

Moisture content (mass %)=[(mass (g) before being dried−mass (g) after being dried)/mass (g) before being dried]×100

Solid content (mass %)=100−moisture content (%)

<Centrifugal Retention Capacity (CRC)>

0.20 g of water absorbent resin particles (water absorbent resin) was evenly contained in a bag (85 mm×60 mm) made of a nonwoven fabric (Heatron Paper made by Nangoku Pulp Kogyo Co., Ltd.: model type is GSP-22). Then, the bag was sealed. Thereafter, the bag was soaked in an excessively large amount (generally, about 500 ml) of 0.9 mass % physiological saline whose temperature had been adjusted to room temperature, and was withdrawn 30 minutes later. By using a centrifugal separator (centrifugal machine made by KOKUSAN Corporation: model type is H-122), the bag was drained for three minutes at a centrifugal force recited in edana ABSORBENCY II 441, 1-99, and a mass W1 (g) of the bag was measured. Further, the same operation was performed without using the water absorbent resin particles, and a mass W0 (g) was measured. Then, from the masses W1 and W0, a centrifugal retention capacity (CRC) [The CRC was evaluated as absorbency measured under no pressure for 30 minutes using a 0.90 mass % physiological saline solution] (g/g) was calculated according to the following equation.

Centrifugal retention capacity (g/g)=(mass W1 (g)−mass W0 (g))/(mass (g) of water absorbent resin particles or water absorbent)−1

<Absorbency Against Pressure (AAP)>

Figure 3:
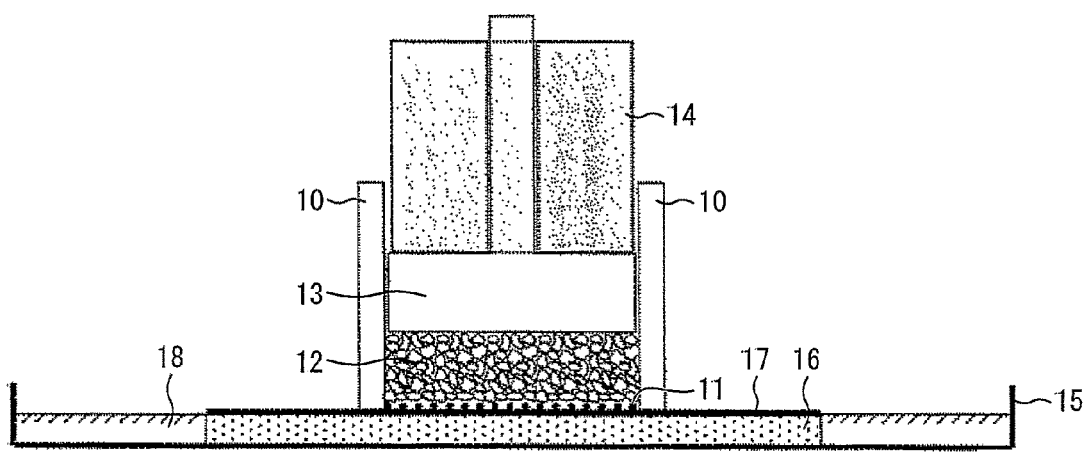
FIG. 3 is a cross sectional view schematically illustrating a measuring device used to measure an absorbency against pressure (AAP) of 4.83 kPa with respect to 0.90 mass % physiological saline in 60 minutes.

By using an apparatus shown in FIG. 3, the absorbency against pressure (AAP) was measured. On a bottom of a plastic supporting cylinder 10 having a 60 mm internal diameter, a metal gauze 11 of stainless-steel 400 mesh (mesh size of 38 μm) was fusion-bonded. Then, under a condition of a room temperature (20° C. to 25° C.) and 50 RH % relative humidity, 0.90 g of water absorbent resin particles (water absorbent resin 12) was evenly spread on the mesh. Subsequently, a piston 13 and a load 14 were placed in this order on the water absorbent resin particles. External diameters of the piston 13 and the load 14 were slightly smaller than 60 mm which was the internal diameter of the supporting cylinder 10, so that there is no gap between the piston and the supporting cylinder, and upward and downward movements of the piston 13 and the load 14 would not be hampered. Note that, the piston 13 and the load 14 were so adjusted as to evenly apply a 4.83 kPa (0.7 psi) load onto the water absorbent resin particles. Then, a mass Wa (g) of this measurement set was measured.

Inside a petri dish 15 having a 150 mm diameter, a glass filter 16 (product of Sougo Rikagaku Glass Seisakusho Co., Ltd.; diameter of fine pores: 100 μm to 120 μm) having a 90 mm diameter was placed. Thereafter, a 0.90 mass % of sodium chloride solution 18 whose temperature had been adjusted to 20° C. to 25° C. was added until it reached a level of an upper surface of the glass filter 16. Then, a piece of filter paper (product of Advantec Toyo Kaisha, Ltd.; product name: JIS P3801, No. 2; thickness: 0.26 mm; diameter of retained particles: 5 μm) having a 90 mm diameter was placed thereon, so that an entire surface of the filter paper 17 was wetted. An excess of the 0.90 mass % saline 18 was removed.

The measuring apparatus set was placed on the wet filter paper 17. Then, the water absorbent resin particles were made to absorb the 0.90 mass % saline 18 for one hour under the load of 4.83 kPa (0.7 psi). One hour later, the measuring apparatus set having absorbed the 0.90 mass % saline 18 was lifted, and a mass Wb (g) thereof was measured. From the masses Wa and Wb, the absorbency against pressure (AAP) (g/g) was calculated according to the following equation.

Absorbency against pressure (g/g)=(Wb (g)−Wa (g))/ mass (0.900 g) of water absorbent resin particles <Saline Flow Conductivity (SFC)>

The 0.69 mass % saline flow conductivity (SFC) is a value indicative of liquid permeability when water absorbent resin particles (water absorbent resin) are swollen. The higher the SFC is, the higher the liquid permeability is.

Calculation of the saline flow conductivity was performed in accordance with a saline flow conductivity (SFC) test recited in Published Japanese Translations of International Publication of Patent Application No. 509591/1997 (Tokuhyohei 9-509591). By using an apparatus shown in FIG. 4, the water absorbent resin particles (0.900 g) evenly spread in a container 40 was swollen in a synthesized urine (1) under a pressure of 0.3 psi (2.07 kPa) for 60 minutes, and a height of a gel layer of a gel 44 was recorded. Then, 0.69 mass % sodium chloride solution 33 was made to flow from a tank 31 and to pass through the swollen gel layer at a constant hydrostatic pressure. The SFC test was performed at room temperature (20 to 25° C.). By using a computer and a scale, an amount of liquid passing through the gel layer at intervals of 20 seconds was recorded for 10 minutes as a time function. A flow rate Fs(T) of the solution passing through the swollen gel 44 (mainly between particles thereof) was determined in terms of g/s by dividing an increasing weight (g) by an increasing time (s). A time in which a constant hydrostatic pressure and a stable flow rate had been obtained was set as "Ts", and only data obtained between "Ts" and a 10-minute interval was used to calculate the flow rate, the flow rate calculated between "Ts" and a 10-minute interval was used to calculate a value of Fs (T=0), i.e., a first flow rate of the solution passing through the gel layer. Fs (T=0) was calculated by extrapolating T=0 from a result obtained by approximating a function indicative of a relationship between Fs (T) and T.

Saline flow conductivity $(SFC)=(Fs(t=0) \times L0)/(\rho \times A \times \Delta P)=(Fs(t=0) \times L0)/139506$ Here, Fs (t=0): a flow rate represented by "g/s"

L0: a height of the gel layer that is represented by "cm"

ρ: a density (1.003 g/cm$^3$) of NaCl solution

A: an area (28.27 cm$^2$) on the upper side of the gel layer of the cell 41

ΔP: a hydrostatic pressure (4920 dyne/cm$^2$) exerted to the gel layer. Further, a unit of the saline flow conductivity (SFC) is $(10^{-7} \cdot cm^3 \cdot s \cdot g^{-1})$.

Figure 4:
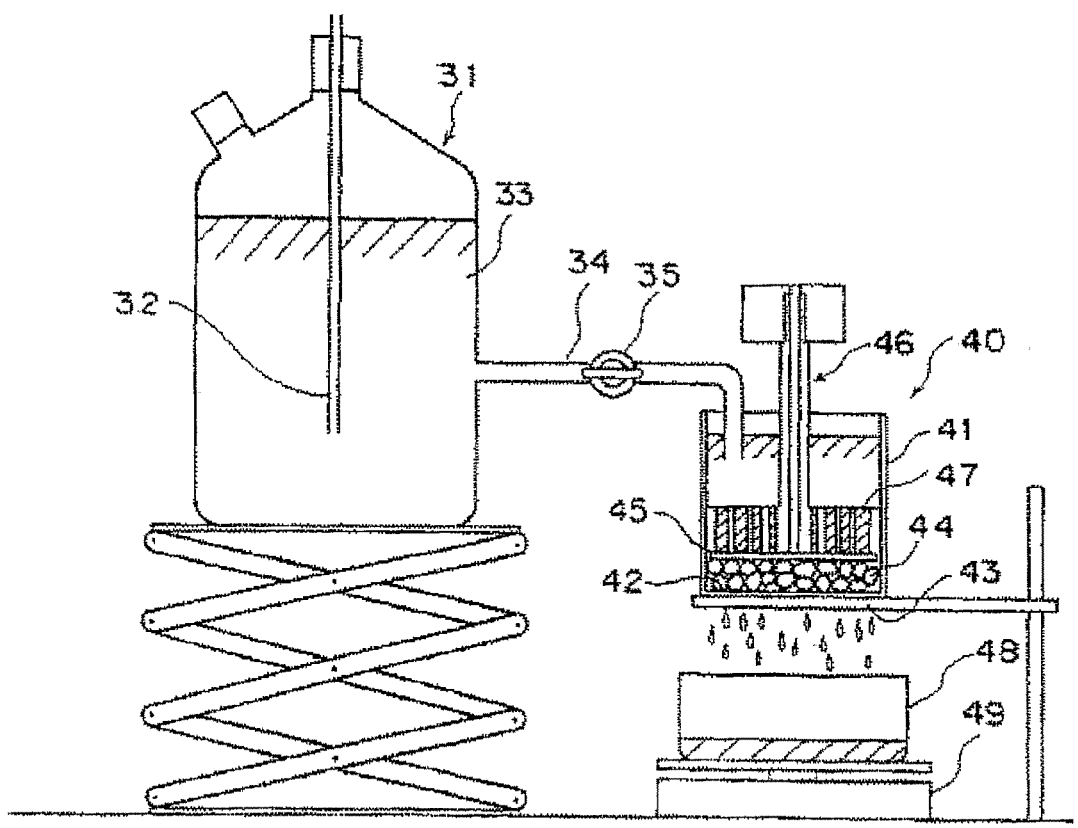
FIG. 4 is a cross sectional view schematically illustrating a measuring device used to measure a saline flow conductivity (SFC) of 0.69 mass % of physiological saline.

In the apparatus shown in FIG. 4, a glass tube 32 was inserted into the tank 31, and a lower end of the glass tube was disposed so that 0.69 mass % sodium chloride solution 33 was positioned 5 cm higher than a bottom of the swelling gel 44 in the cell 41. 0.69 mass % sodium chloride solution 33 contained in the tank 31 was supplied to the cell 41 via an L-shaped tube 34 with a cock 35. A collecting container 48 for collecting liquid having passed through the gel layer was disposed under the cell 41, and the collecting container 48 was placed on an even balance 49. An inside diameter of the cell 41 was 6 cm, and No. 400 stainless metal gauze (38 μm in mesh) 42 was placed on a bottom of a lower portion of the cell 41. A hole 47 which allowed liquid to pass through was provided on a lower portion of a piston 46, and a glass filter 45 having high permeability was provided on the bottom thereof so that (i) the water absorbent resin particles or the water absorbing agent or (ii) the swelling gel did not enter into the hole 47. The cell 41 was placed on a table for the cell, and the table's surface which is in contact with the cell was positioned on the stainless metal gauze 43 which did not prevent the liquid from passing through.

The synthesized urine (1) was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of pure water.

<Mass Average Particle Diameter (D50) And Logarithmic Standard Deviation (σζ) of Particle Size Distribution>

The mass average particle diameter (D50) and the logarithmic standard deviation (σζ) of particle size distribution were calculated in accordance with the mass average particle diameter (D50) test and the particle size distribution logarithmic standard deviation (σζ) test which are described in International Publication No. 2004/69915 pamphlet.

<Ratio of Particles Passing Through a Sieve Whose Mesh Size is 150 μm>

The same classification operation was carried out as in the measurement of the mass average particle diameter (D50) and the logarithmic standard deviation (σζ) of particle size distribution. In accordance with an amount of particles having passed through the sieve whose mesh size is 150 μm, a ratio (mass %) of particles passing through a sieve whose mesh size is 150 μm was calculated.

<Rate of Increase of Fine Powder in Receiving Shock>

30 g of water absorbent resin whose particle diameter ranged from 150 to 850 μm and 10 g of glass beads (soda glass) whose diameter was 6 mm were taken to a 225 ml mayonnaise bottle with a lid. The bottle was set in a paint shaker (product of TOYO SEIKI Seisakusho), and were shaken for 10 minutes. Thereafter, an amount (mass %) of produced particles (fine powder, powder) whose particle diameter was 9 μm or less was measured. As the measured value is smaller, fine powder is less likely to be reproduced at the time of shock and the particle structure is stronger.

<Shape of Bound Particle>

Hydrous particles (bound particles) of the water absorbent resin powder were retrieved and dried in a hot air dryer at 170° C. for 60 minutes, and a shape of each particle of the dried resultant was checked with eyes. Next, about 100 particles thereof were retrieved and particle diameters of the particles were measured with a ruler (micrometer calipers) and an average particle diameter (mm) thereof was calculated.

Reference Example 1

In a kneader (LDS-50-0V produced by Koike Seisakusho) equipped with two sigma blades, monomer aqueous solution (monomer concentration was 39 wt % and neutralization rate was 75 mol %) made of sodium acrylate aqueous solution, acrylic acid, and water was prepared, and polyethyleneglycol diacrylate (average ethyleneoxide unit number was 9) was dissolved in the monomer aqueous solution so that its concentration was 0.045 mol % (with respect to the monomer).

Then, nitrogen gas was injected into the monomer aqueous solution so as to reduce dissolved oxygen in the monomer aqueous solution and so as to replace an internal air of the kneader with nitrogen entirely. Subsequently, cold water of 10° C. was circulated in the jacket while rotating the blades of the kneader, thereby adjusting temperature of the monomer aqueous solution to 20° C.

Subsequently, 0.05 mol % (with respect to the monomer) of sodium persulfate and 0.003 mol % (with respect to the monomer) of L-ascorbic acid were added as polymerization initiator so as to initiate polymerization, and the resultant was stirred for 30 minutes, thereby obtaining a hydrogel polymer whose average particle diameter was about 2.0 mm as the polymer.

The resultant hydrogel polymer was dried in a hot air dryer (SATAKE parallel batch type dryer 71-S6 produced by SATAKE CORPORATION) at 170° C. for 60 minutes. The dried resultant was roughly fragmented and then was spread out on a wire mesh of 850 μm sieve (JIS standard sieve). Subsequently, the dried resultant on the sieve was pulverized by a roll mill and then classified by using a JIS standard sieve whose mesh size was 850 μm and a JIS standard sieve whose mesh size was 180 μm. The dried resultant which has not passed through the 850 μm sieve was pulverized again by the roll mill and then was classified in the foregoing manner. An amount of the dried resultant having been classified by the 180 μm sieve was about 15 wt % with respect to a total amount of the dried resultant.

As to water absorbent resin particles (A) obtained by the foregoing classification, its absorbency was 38 g/g, its average particle diameter was 420 μm, and an amount of powder included therein and having a particle diameter of 150 μm or less was 3 wt %.

Example 1

7 L (Stirring Section has an Effective Volume of 5 L) Vertical Rotation Disk Mixer, Solid Content was 67 wt %, an Amount of Introduced Steam at 0.6 MPa was 15 kg/hr There was used a vertical rotation disk mixer (product of FUNKEN POWTECH INC.), which was equipped with stirring vanes, fragmentation vanes, discharging vanes, and nozzles, and whose internal volume was 7 L, and water absorbent resin powder (a) having passed through the 180 μm sieve used in the classification of Reference Example 1 was supplied at 100 kg/hr by using a volumetric feeder (product of Accurate Inc.) and was rotated by the stirring vanes, thereby continuously mixing the water absorbent resin powder (a) with water poured at 42.9 kg/h in a mixer (improved version of continuous flow jet mixer MW-F-300 (a pin had been removed from its rotation disk) produced by FUNKEN POWTECH INC.) while injecting moisture vapor (gage pressure was 0.6 MPa and the mixer was free from any internal pressure) into the mixer at 15 kg/h.

Note that, as to the water absorbent resin powder (a), its absorbency was 37 g/g, its average particle diameter was 88 μm, and an amount of particles having passed through the 150 μm sieve was about 80 wt %.

After the mixture, hydrous water absorbent resin powder (bound particles) was retrieved from the mixer. Note that, a moisture content of the hydrous power retrieved after the mixture was 33%. Subsequently, the retrieved resultant was dried for 60 minutes in a hot air dryer at 170° C., and the dried resultant was pulverized and classified as in Reference Example 1.

As to water absorbent resin particles (a1) obtained by the classification, its absorbency was 37 g/g, its average particle diameter was 400 μm, and an amount of powder whose particle diameter was 150 μm or less was 11 wt %.

Further, a rate of increase of fine powder in receiving a shock was 2.4%.

FIG. 1 shows variation of a solid content of the water absorbent resin when the hydrous water absorbent resin powder (bound particles) was retrieved after the mixture and the retrieved resultant was dried for 60 minutes in the hot air dryer at 170° C.

Figure 2:
FIG. 2 is a schematic illustrating an exterior view of water absorbent resin obtained according to the method for binding water absorbent resin, and (a) illustrates an exterior view of water absorbent resin obtained according to an embodiment of the method of the present invention for binding water absorbent resin, and each of (b) and (c) illustrates an exterior view of water absorbent resin obtained according to the conventional method for binding water absorbent resin.
Figure 2:
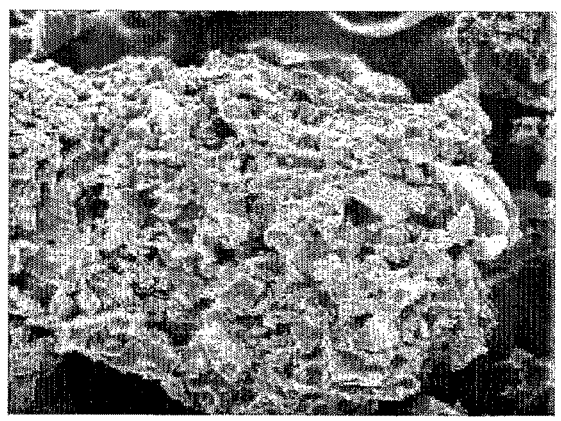
Figure 2:
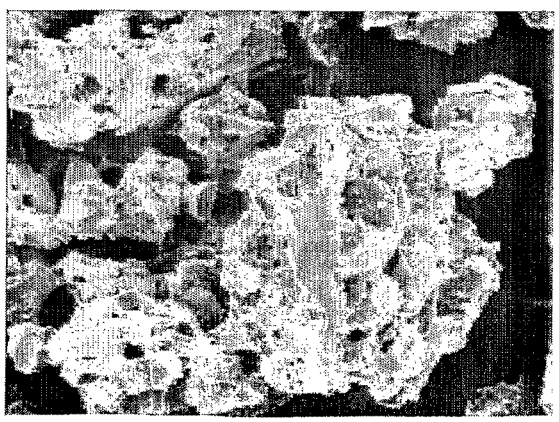

FIG. 2(a) shows an external view of the water absorbent resin of Example 1. As shown in FIG. 2(a), there is no void in the water absorbent resin obtained by adding water and moisture vapor to highly concentrated water absorbent resin powder (solid content was 70 wt %). As a result, the water absorbent resin has excellent damage resistance.

Example 2

7 L (Stirring Section has an Effective Volume of 5 L) Vertical Rotation Disk Mixer, Solid Content was 66 wt %, an Amount of Introduced Steam at 0.6 MPa (Free from any Mixer Internal Pressure) was 30 kg/hr The same operation as in Example 1 was carried out except that the moisture vapor was injected at 30 kg/hr in being mixed with the water absorbent resin powder (a), thereby obtaining water absorbent resin particles (2). Note that, a moisture content of the hydrous resultant retrieved after the mixture was 34%.

As to resultant water absorbent resin particles (a2), its absorbency was 37 g/g, its average particle diameter was 400 μm, and an amount of powder whose particle diameter was 150 μm or less was 11 wt %.

Further, a rate of increase of fine powder in receiving a shock was 2.0%.

Example 3

Figure 5:
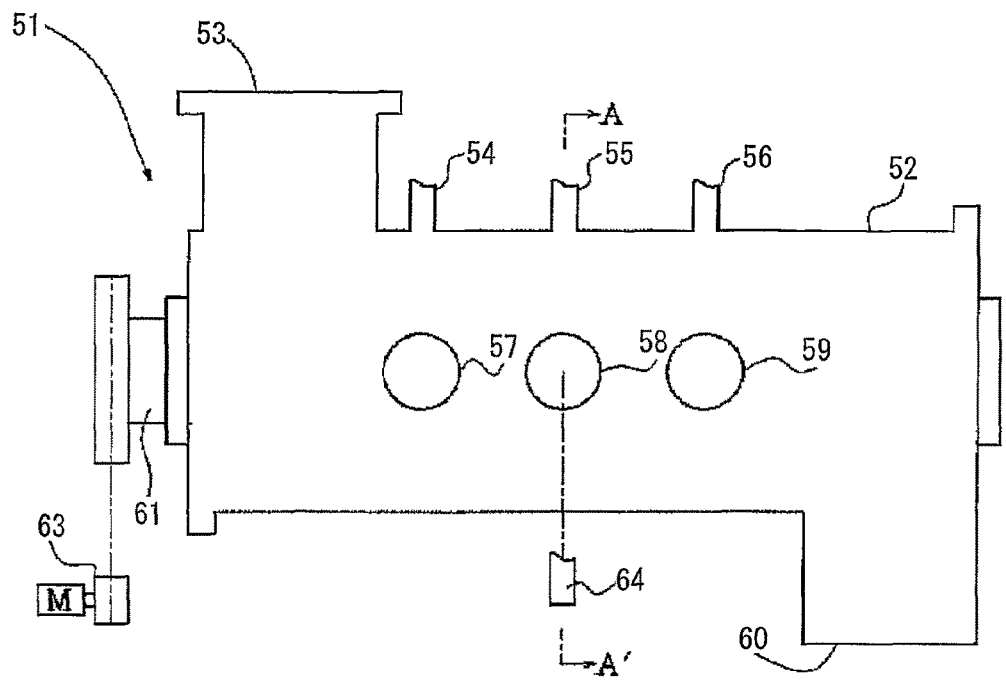
FIG. 5 is a plan view of a horizontal continuous mixer used in an embodiment of the method of the present invention for binding water absorbent resin.
Figure 6:
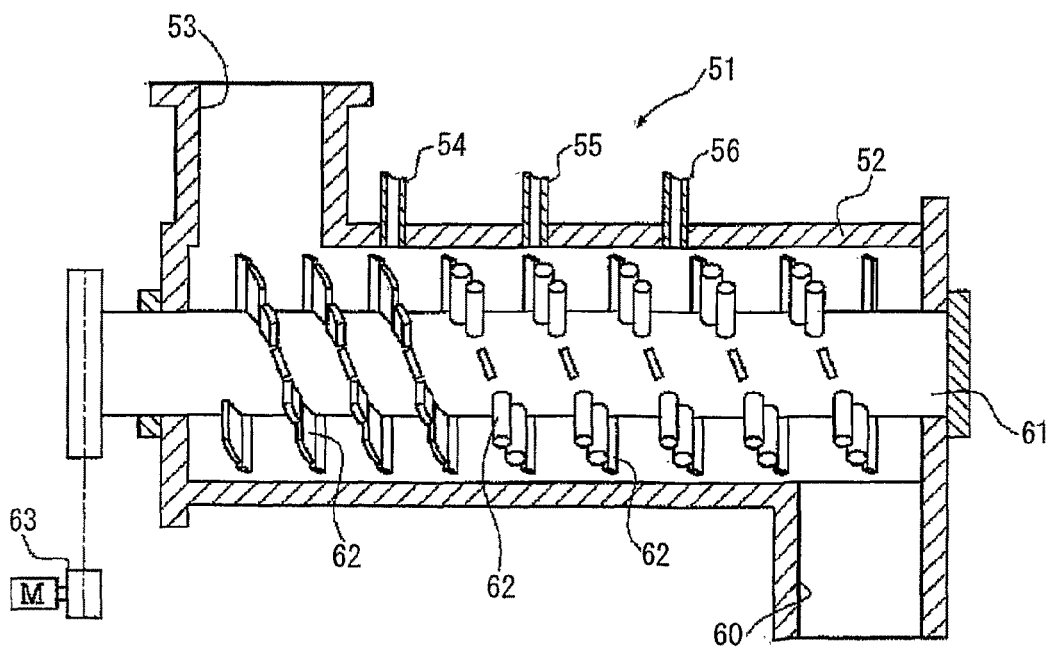
FIG. 6 is a cross sectional view of the horizontal continuous mixer used in an embodiment of the method of the present invention for binding water absorbent resin.

Horizontal Continuous Mixer, Solid Content was 67 wt %, an Amount of Introduced Steam at 0.6 MPa (Free from any Mixer Internal Pressure) was 15 kg/hr A horizontal continuous mixer 51 shown in FIG. 5 and FIG. 6 was used. Air was supplied via an inlet 53 provided on one end of the horizontal continuous mixer (continuous extrusion mixer) 51, that is, provided on a left end in FIG. 5. An internal pressure of the horizontal continuous mixer 51 was kept at a reduced pressure not higher than 5 mm $H_2O$. In this state, water was supplied at 47 kg/hr via an inlet 54 positioned away from a left end of the casing 52 by 140 mm under such condition that a total length of a rotational axis 61 existing in the casing 52 was 475 mm. Further, continuous mixture was carried out while supplying moisture vapor (gage pressure was 0.6 MPa, free from any mixer internal pressure) at 15 kg/hr via an inlet 55 positioned away from the left end of the casing 52 by 230 mm.

While, a volumetric feeder (product of Accurate Inc.) was used to supply, to the horizontal continuous mixer 51, the water absorbent resin powder (a), obtained in Reference Example 1, at 110 kg/hr via an inlet 58 positioned away from a left end of the rotational axis 61 in the casing 52 by 228 mm (about 52% downstream with respect to an outlet 60 under such condition that the total length of the rotational axis 61 was 100%), and a stirring vane 62 was rotated at 1700 rpm, thereby continuously mixing the water absorbent resin powder (a) with water/moisture vapor.

As a result, from the outlet 60 positioned on a right end of the horizontal continuous mixer 51, bound particles whose particle diameter ranged from 2 mm to 5 mm were continuously obtained.

After the mixture, hydrous particles of the water absorbent resin powder were retrieved from the mixer and dried in a hot air dryer at 170° C. for 60 minutes, and the dried resultant was pulverized and classified as in Reference Example 1. Note that, a moisture content of the hydrous particles retrieved after the mixture was 33%.

As to water absorbent resin particles (a3) obtained by the classification, its absorbency was 37 g/g, its average particle diameter was 400 μm, and an amount of powder whose particle diameter was 150 μm or less was 14 wt %. Further, a rate of increase of fine powder in receiving a shock was 2.4%.

Example 5

7 L (Stirring Section has an Effective Volume of 5 L) Vertical Rotation Disk Mixer, Solid Content was 86 wt %, an Amount of Introduced Steam at 0.6 MPa (Free from any Mixer Internal Pressure) was 15 kg/hr The same operation as in Example 1 was carried out except that 0.10 wt % of sodium persulfate (with respect to the water absorbent resin powder (a)) was added into 390 kg/hr of the water absorbent resin powder (a) and 42.9 kg/hr of water, thereby obtaining water absorbent resin particles (a5). Note that, a moisture content of hydrous particles retrieved after the mixture was 14%.

Next, a solution (A) was prepared by mixing 288.2 g of acrylic acid, 0.29 g of polyethyleneglycoldiacrylate (average molecular weight was 522) serving as an internal crosslinking agent, and 1.8 g of 1 mass % diethylenetriamine penta acetic acid penta sodium salt aqueous solution serving as a chelating agent, in a 1 L polypropylene resin container. Further, a solution (B) was prepared by mixing 230.9 g of 48.5 mass % sodium hydroxide aqueous solution with 129.1 g of ion exchange water. Subsequently, the solution (B) was quickly added to and mixed with the solution (A) while being stirred at 500 rpm by a magnetic stirrer chip whose length was 50 mm, thereby obtaining a monomer aqueous solution (C). Due to neutralization heat and dissolution heat, a temperature of the monomer aqueous solution (C) rose to 102° C.

When the temperature of the monomer aqueous solution (C) was decreased to 96° C., 90 g of the water absorbent resin particles (a5) were added to thus obtained monomer aqueous solution (C), and 11 g of 3 mass % sodium persulfate aqueous solution was subsequently added to the monomer aqueous solution (C), and the mixture was stirred for about 1 second. Thereafter, the resultant was poured in an open manner into a stainless tray-type container whose surface was heated up to 130° C. by a hot plate (NEO HOTPLATE H1-1000: product of IUCHI SEIEIDO CO., LTD.). The stainless tray-type container was internally coated with teflon (registered trademark), and its bottom size was 250×250 mm.

Polymerization was initiated right after the monomer aqueous solution had been poured. The polymerization was promoted while generating moisture vapor (polymerization initiation temperature was 97° C.). Within about 1 minute after the polymerization, the temperature became a peak temperature (peak temperature was 106° C.). 3 minutes later, a hydrous polymer (hydrogel) was retrieved. Note that, a series of these operations were carried out in an open manner.
<Gel Fragmentation>

The retrieved hydrogel crosslinked polymer was cut into strips each having a width of 100 mm with scissors, and then the resultant strips were crushed with an upright crusher (model type: VM27-S, product of Orient, 8 mm screen), thereby obtaining particulate hydrous polymer (D) having fluidity.
<Drying, Pulverization, and Classification>

After the fragmentation, the particulate hydrous polymer (D) was retrieved and dried in a hot air dryer at 170° C. for 60 minutes, and the dried resultant was pulverized and classified as in Reference Example 1, thereby obtaining water absorbent resin. As to the resultant water absorbent resin, its solid content was 96 wt %, its absorbency was 36, its average particle diameter was 440 μm, a content of powder whose particle diameter was 150 μm or less was 7 wt %, and has an indefinitely pulverized shape. Further, a rate of increase of fine powder is receiving a shock was 1.8%.

Comparative Example 1

7 L (Stirring Section has an Effective Volume of 5 L) Vertical Rotation Disk Mixer, Solid Content was 68 wt %, No Steam The same operation as in Example 1 was carried out except that the moisture vapor was not used, thereby obtaining water absorbent resin particles (c1). Note that, a moisture content of the hydrous resultant retrieved after the mixture was 32%.

As to resultant water absorbent resin particles (c1), its absorbency was 37 g/g, its average particle diameter was 400 μm, and an amount of powder whose particle diameter was 150 μm or less was 18 wt %.

Further, a rate of increase of fine powder in receiving a shock was 4.0%.

FIG. 1 shows variation of a solid content of the water absorbent resin when the hydrous water absorbent resin powder (bound particles) was retrieved after the mixture and the retrieved resultant was dried for 60 minutes in the hot air dryer at 170° C.

FIG. 2(b) shows an external view of the water absorbent resin of Comparative Example 1. As shown in FIG. 2(b), there are voids in the water absorbent resin obtained by adding water and moisture vapor to highly concentrated water absorbent resin powder (solid content was 70 wt %). As a result, the water absorbent resin is inferior in the damage resistance.

Comparative Example 2

5 L Mortar Mixer, Solid Content was 42 wt %, No Steam, a Time Taken to Carry out Stirring/Mixture was 60 Seconds A 5 L mortar mixer (product of Nishinihon Shikenki, rotational motion was 280 rpm, orbital motion was 125 rpm) was used, and 100 parts of the water absorbent resin powder (a) having passed through the 180 μm sieve used in the classification of Reference Example 1 and 110 parts of hot water whose temperature was about 90° C. were mixed for 60 seconds while being stirred.

After the mixture, hydrous water absorbent resin powder was retrieved from the mixer, and the retrieved resultant was dried for 50 minutes in a hot air dryer at 180° C., and the dried resultant was pulverized and classified as in Reference Example 1. Note that, a moisture content of the hydrous powder retrieved after the mixture was 58%.

As to water absorbent resin particles (c2) obtained by the classification, its absorbency was 35 g/g, its average particle diameter was 390 μm, and an amount of powder whose particle diameter was 150 μm or less was 15 wt %.

Further, a rate of increase of fine powder in receiving a shock was 3.5%.

FIG. 1 shows variation of a solid content of the water absorbent resin when the hydrous water absorbent resin powder (bound particles) was retrieved after the mixture and the retrieved resultant was dried for 60 minutes in the hot air dryer at 170° C.

FIG. 2(c) shows an external view of the water absorbent resin of Comparative Example 2. As shown in FIG. 2(c), there are voids in the water absorbent resin obtained by adding water and moisture vapor to less concentrated water absorbent resin powder (solid content was 42 wt %). As a result, the water absorbent resin is inferior in the damage resistance.

Comparative Example 3

7 L (Stirring Section has an Effective Volume of 5 L) Vertical Rotation Disk Mixer, Solid Content was 93 wt %, an Amount of Introduced Steam at 0.6 MPa (Free from any Mixer Internal Pressure) was 15 kg/hr The same operation as in Example 1 was carried out except that the aqueous liquid was not used, thereby obtaining water absorbent resin particles. The resultant water absorbent resin powder was powdery. Note that, a moisture content of the hydrous resultant retrieved after the mixture was 7%.

Example 4

Subjected to a Surface Crosslinking Treatment after Example 1

30 parts of the hydrous water absorbent resin powder (a) of Example 1 and 250 parts of the hydrogel polymer of Reference Example 1 were dried for 60 seconds in a hot air dryer at 170° C. The dried resultant was pulverized and classified as in Reference Example 1, thereby obtaining water absorbent resin particles (4).

As to resultant water absorbent resin particles (a4), its absorbency was 38 g/g, its average particle diameter was 420 µm, and an amount of powder whose particle diameter was 150 µm or less was 3 wt %.

3.3 parts of a composition liquid made of propyleneglycol, butanediol, and water was sprayed so as to be mixed with 100 parts of the water absorbent resin particles (a4). Note that, a composition ratio (mass ratio) of the components in the composition liquid was such that propyleneglycol/butanediol/water=0.3/0.5/2.5. The resultant mixture was heated at 200° C. for 40 minutes while being stirred, thereby obtaining surface-crosslinked water absorbent resin particles (a4-1).

Further, as to the surface-crosslinked water absorbent resin particles (a4-1), its absorbency was 38 g/g and its absorbency against pressure was 24 g/g. Further, its saline flow conductivity (SFC) was $50(10^{-7} \cdot cm^3 \cdot s \cdot g^{-1})$.

Comparative Example 4

Subjected to a Surface Crosslinking Treatment after Comparative Example 1

The same operation as in Example 4 was carried out except that 30 parts of the hydrous water absorbent resin powder of Comparative Example 1 was used instead of 30 parts of the hydrous water absorbent resin powder of Example 1, thereby obtaining water absorbent resin particles (c5) and surface-crosslinked water absorbent resin particles (c5-1). As to the resultant water absorbent resin particles (c5), its absorbency was 38 g/g, its average particle diameter was 420 µm, and an amount of powder whose particle diameter was 150 µm or less was 5 wt %.

Further, as to the surface-crosslinked water absorbent resin particles (c5-1), its absorbency was 38 g/g and its absorbency against pressure was 20 g/g. Further, its saline flow conductivity (SFC) was $45(10^{-7} \cdot cm^3 \cdot s \cdot g^{-1})$.

Table 1 shows evaluation results of Examples 1 to 5 and Comparative Examples 1 to 4.

TABLE 1

| | Aqueous liquid to be added | Amount of moisture vapor to be added | Moisture content (%) | Absorbency (g/g) | Average particle diameter (µm) | Ratio (wt %) of particles whose particle diameter is 150 µm or less | Rate (wt %) of increase of fine powder in receiving shock | Shape of each bound particle |
|---|---|---|---|---|---|---|---|---|
| Example 1 | water | 15 kg/hr | 33 | 37 | 400 | 13 | 2.4 | Spherical Shape of 4.0 mm |
| Example 2 | water | 30 kg/hr | 34 | 37 | 400 | 11 | 2.0 | Spherical shape of 4.2 mm |
| Comparative Example 1 | water | no moisture vapor | 32 | 37 | 400 | 18 | 4.0 | Indefinite shape of about 0.1 to 5.0 mm (unable to be separated as clump) |
| Comparative Example 2 | hot water | no moisture vapor | 58 | 35 | 390 | 15 | 3.5 | Indefinite shape of about 0.05 to 6.0 mm (unable to be separated as clump) |
| Comparative Example 3 | no aqueous liquid | 15 kg/hr | 7 | unable to bind | unable to bind | 78 (unbound particles) | unable to bind | Fine-powdery state |
| Example 4 | water | 15 kg/hr | — | 38 | 420 | 3 | — | — |
| Comparative Example 4 | water | no moisture vapor | — | 38 | 420 | 5 | — | — |
| Example 3 | water | 15 kg/hr | 33 | 37 | 400 | 14 | 2.4 | Polygonal shape of |

TABLE 1-continued

|  | Aqueous liquid to be added | Amount of moisture vapor to be added | Moisture content (%) | Absorbency (g/g) | Average particle diameter (μm) | Ratio (wt %) of particles whose particle diameter is 150 μm or less | Rate (wt %) of increase of fine powder in receiving shock | Shape of each bound particle |
|---|---|---|---|---|---|---|---|---|
| Example 5 | water | 15 kg/hr | 14 | 36 | 440 | 7 | 1.8 | 3.5 mm Irregularly spherical shape of 4.0 mm |

Conclusion of Examples

As shown in Table 1, Example 1 and Comparative Example 1 were compared as follows. As to the water absorbent resin particles (a1) of Example 1, the amount of powder whose particle diameter was 150 μm or less was 13 wt %, and the rate of increase of fine powder in receiving a shock was 2.4%. On the other hand, as to the water absorbent resin particles (c1) of Comparative Example 1, the amount of powder whose particle diameter was 150 μm or less was 18 wt %, and the rate of increase of fine powder in receiving a shock was 4.0%. As a result, the comparison shows that, by adding water and moisture vapor to the water absorbent resin powder, fine powder hardly occurs in receiving a shock and has a strong particle structure and excellent damage resistance, unlike the case where only water is added.

Further, as shown in Table 1, Example 1 and Comparative Example 3 were compared as follows. As to the water absorbent resin particles (a1) of Example 1, particles which do not impair the handling property were generated. On the other hand, the water absorbent resin powder of Comparative Example 3 were unbound particles which impair the handling property. As a result, the comparison shows that, by adding water and moisture vapor to the water absorbent resin powder, the cohesive force is enhanced, unlike the case where only moisture vapor is added.

Further, as shown in Table 1, a time taken for the solid content of the water absorbent resin particles (a1) of Example 1 to attain 92 wt % was about 15 minutes, and a time taken for the solid content of the water absorbent resin particles (c1) of Example 1 to attain 92 wt % was about 45 minutes. As a result, the comparison shows that, by adding water and moisture vapor to the water absorbent resin powder, the drying time in producing the water absorbent resin particles is about ⅓, unlike the case where only water is added.

As described above, a method of the present invention for binding particulate water absorbent resin includes the step of adding aqueous liquid and moisture vapor to water absorbent resin powder so as to bind particles of the water absorbent resin powder.

As described above, a method of the present invention for producing particulate water absorbent resin includes the step of adding aqueous liquid and moisture vapor to water absorbent resin powder so as to bind particles of the water absorbent resin powder.

Therefore, the water absorbent resin is highly concentrated, that is, the solid content of the water absorbent resin is increased, so that it is possible to provide (i) a method for binding (granulating) water absorbent resin and (ii) a method including the step of binding (granulating) particles of water absorbent resin powder so as to produce particulate water absorbent resin, each of which methods makes it possible to improve the drying efficiency and makes it possible to obtain highly concentrated water absorbent resin, i.e., particulate water absorbent resin having excellent property even in case where the solid content of the water absorbent resin is large.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The method of the present invention for binding water absorbent resin and the method of the present invention for producing particulate water absorbent resin are favorably applicable to production of particulate water absorbent resin used to constitute a sanitary material such as a disposable diaper, a sanitary napkin, an incontinence pad, and the like, whose object is to absorb aqueous liquid such as body fluid or used to constitute a water absorbent material for horticulture, agriculture, and the like. Further, these methods are favorably applicable also to the case of additionally using water absorbent resin powder, having removed in the water absorbent resin production steps, in a predetermined step of the water absorbent resin production steps. Further, the method of the present invention for binding water absorbent resin and the method of the present invention for producing particulate water absorbent resin are applicable also to a mass production plant.

The invention claimed is:

1. A method for binding water absorbent resin, comprising the step of adding aqueous liquid and adding saturated moisture vapor to water absorbent resin powder so as to bind particles of the water absorbent resin powder, where the aqueous liquid and saturated moisture vapor are added at the same time to the water absorbent resin powder, and wherein 50 to 10 parts by weight of the aqueous liquid is added to 50 to 90 parts by weight of the water absorbent resin powder so that a total amount is 100 parts, the water absorbent resin powder containing an acid group and/or its salt (neutralized product), and the water absorbent resin powder including 10 wt % or less of water with respect to the total weight of the water absorbent resin.

2. The method as set forth in claim 1, wherein the particles of the water absorbent resin powder are continuously bound.

3. The method as set forth in claim 1, wherein 1 to 100 kg/hr of the saturated moisture vapor is added to 100 kg/hr of the water absorbent resin powder.

4. The method as set forth in claim 1, wherein the particles of the water absorbent resin powder are bound by using a rotary disk mixer.

5. The method as set forth in claim 1, wherein the water absorbent resin powder includes powder of water absorbent resin whose surface has been crosslinked.

6. A method for producing particulate water absorbent resin, comprising the step of adding aqueous liquid and adding saturated moisture vapor to water absorbent resin powder so as to bind particles of the water absorbent resin powder, where said aqueous liquid and saturated moisture vapor are added at the same time to the water absorbent resin powder, the water absorbent resin powder containing an acid group and/or its salt (neutralized product), and the water absorbent resin powder including 10 wt % or less of water with respect to the total weight of the water absorbent resin, and wherein a solid content of the water absorbent resin powder whose particles have been bound ranges from 50 to 90 wt %.

7. The method as set forth in claim 6, comprising plural steps of binding the particles of the water absorbent resin powder.

8. The method as set forth in claim 6, wherein granulated particles are obtained by the binding step, wherein said granulated particles having particle diameter ranges from 100 μm to 40 mm are added in a polymer classification step or in a step previous to a polymer classification step and subjected to a drying step, or where the granulated particles are added in a step previous to a polymer classification step without a drying step.

9. The method as set forth in claim 1, wherein a gage pressure of the saturated moisture vapor ranges from 0.1 to 2.0 MPa.

10. The method as set forth in claim 6, wherein a gage pressure of the saturated moisture vapor ranges from 0.1 to 2.0 MPa.

* * * * *